United States Patent
Arai et al.

(10) Patent No.: US 11,751,836 B2
(45) Date of Patent: Sep. 12, 2023

(54) CONTROL DEVICE, RADIOGRAPHY SYSTEM, MEDICAL IMAGING SYSTEM, CONTROL METHOD, AND CONTROL PROGRAM

(71) Applicant: FUJIFILM Corporation, Tokyo (JP)

(72) Inventors: Takahisa Arai, Kanagawa (JP); Yoshie Fujimoto, Kanagawa (JP); Hiroki Nakayama, Kanagawa (JP); Shunsuke Kodaira, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 569 days.

(21) Appl. No.: 16/857,070

(22) Filed: Apr. 23, 2020

(65) Prior Publication Data
US 2020/0337667 A1    Oct. 29, 2020

(30) Foreign Application Priority Data
Apr. 26, 2019    (JP) .................... 2019-086597

(51) Int. Cl.
*A61B 6/00*    (2006.01)
*A61B 6/04*    (2006.01)
(Continued)

(52) U.S. Cl.
CPC .......... *A61B 6/5247* (2013.01); *A61B 6/0414* (2013.01); *A61B 6/0435* (2013.01);
(Continued)

(58) Field of Classification Search
CPC ... A61B 6/5247; A61B 6/0414; A61B 6/0435; A61B 6/4417; A61B 6/502; A61B 6/54;
(Continued)

(56) References Cited

U.S. PATENT DOCUMENTS

2003/0181801 A1* 9/2003 Lasser ................ A61B 6/4417
                                                                600/407
2006/0034503 A1    2/2006 Shimayama
(Continued)

FOREIGN PATENT DOCUMENTS

EP    3412207 A1    12/2018
JP    2006-051198 A    2/2006
(Continued)

OTHER PUBLICATIONS

The extended European search report issued by the European Patent Office dated Oct. 5, 2020, which corresponds to European Patent Application No. 20170570.4-1122 and is related to U.S. Appl. No. 16/857,070.
(Continued)

*Primary Examiner* — Sean D Mattson
(74) *Attorney, Agent, or Firm* — Studebaker & Brackett PC

(57) ABSTRACT

A control device including: a control unit that, in a case in which continuous imaging that irradiates a breast of a subject with radiation emitted from a radiation source to capture a radiographic image in a compressed state in which the breast is compressed against an imaging table by a compression member and then captures an ultrasound image of the breast in the compressed state is performed, performs control to locate the radiation source at a non-facing position where the radiation source and the imaging table do not face each other.

15 Claims, 17 Drawing Sheets

(51) Int. Cl.
 *A61B 8/08* (2006.01)
 *A61B 8/00* (2006.01)
(52) U.S. Cl.
 CPC ............ *A61B 6/4417* (2013.01); *A61B 6/502* (2013.01); *A61B 6/54* (2013.01); *A61B 6/547* (2013.01); *A61B 8/0825* (2013.01); *A61B 8/403* (2013.01); *A61B 8/406* (2013.01); *A61B 8/5261* (2013.01); *A61B 8/4245* (2013.01); *A61B 8/4416* (2013.01)
(58) Field of Classification Search
 CPC ....... A61B 6/547; A61B 6/025; A61B 8/0825; A61B 8/403; A61B 8/406; A61B 8/5261; A61B 8/4245; A61B 8/4416
 See application file for complete search history.

(56) References Cited

U.S. PATENT DOCUMENTS

| 2008/0075228 | A1* | 3/2008 | Tasaki ................... A61B 6/542 378/37 |
| 2010/0246924 | A1 | 9/2010 | Morita |
| 2012/0029344 | A1* | 2/2012 | Nakayama ........... A61B 8/4416 378/62 |
| 2012/0150034 | A1* | 6/2012 | DeFreitas .............. A61B 8/483 250/363.04 |
| 2012/0245463 | A1 | 9/2012 | Mertelmeier |
| 2014/0135623 | A1* | 5/2014 | Manak ................. A61B 8/5261 600/427 |
| 2017/0281124 | A1 | 10/2017 | Arai et al. |
| 2017/0360389 | A1* | 12/2017 | Ochiai ................... A61B 6/502 |
| 2018/0249985 | A1 | 9/2018 | DeFreitas et al. |
| 2019/0175129 | A1 | 6/2019 | Dueppenbecker et al. |
| 2020/0352543 | A1 | 11/2020 | DeFreitas et al. |

FOREIGN PATENT DOCUMENTS

| JP | 2010-253245 A | 11/2010 |
| JP | 2014-504918 A | 2/2014 |
| JP | 2017-184864 A | 10/2017 |
| JP | 2018-186842 A | 11/2018 |

OTHER PUBLICATIONS

"Notice of Reasons for Refusal" Office Action issued in JP 2019-086597; mailed by the Japanese Patent Office dated Aug. 9, 2022.

* cited by examiner

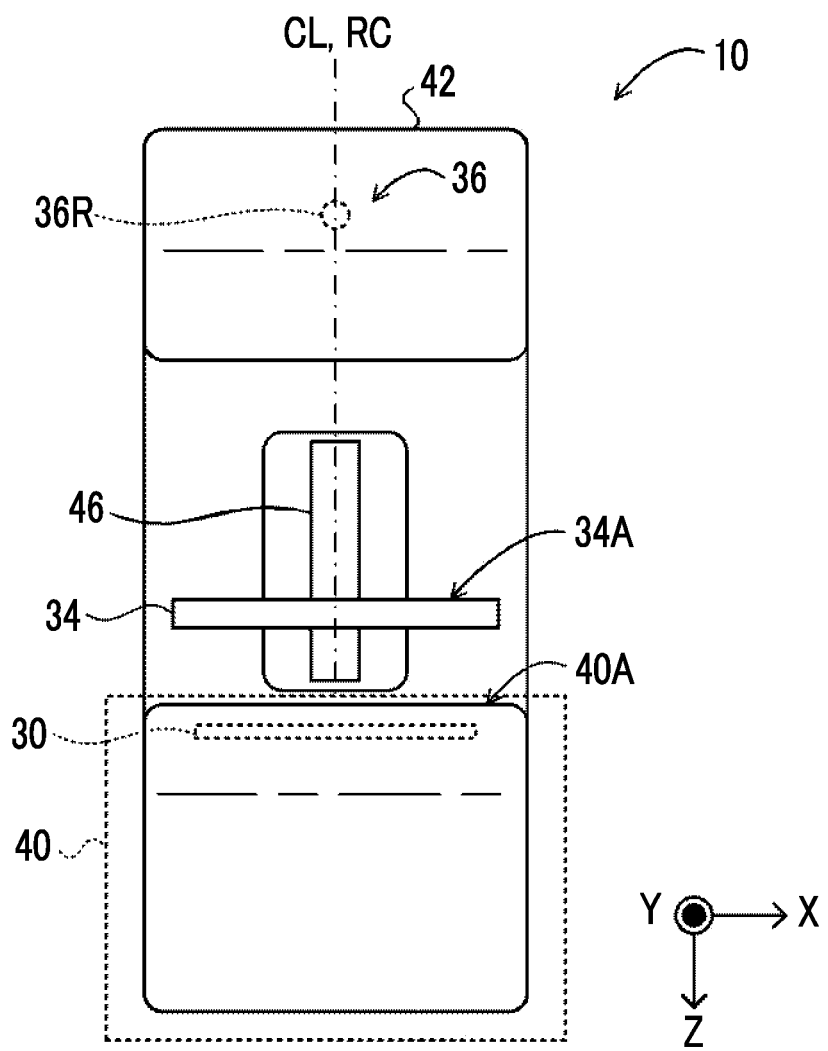

FIG. 17

| TYPE OF IMAGING | POSITION OF ULTRASONOGRAPHY APPARATUS | RETREAT POSITION |
|---|---|---|
| CC IMAGING | LEFT | MLO IMAGING POSITION FOR RIGHT BREAST |
| CC IMAGING | RIGHT | MLO IMAGING POSITION FOR LEFT BREAST |
| MLO IMAGING | -- | CC IMAGING POSITION |
| TOMOSYNTHESIS IMAGING | LEFT | IMAGING POSITION (LAST) |
| TOMOSYNTHESIS IMAGING | RIGHT | IMAGING POSITION (INITIAL) |

| TYPE OF IMAGING | NON-FACING POSITION | |
|---|---|---|
| CC IMAGING | MLO IMAGING POSITION | ~23A |
| MLO IMAGING | CC IMAGING POSITION | |
| TOMOSYNTHESIS IMAGING | IMAGING POSITION (LAST) | |

CONTROL DEVICE, RADIOGRAPHY SYSTEM, MEDICAL IMAGING SYSTEM, CONTROL METHOD, AND CONTROL PROGRAM

CROSS-REFERENCE TO RELATED APPLICATION

The present application claims priority under 35 U.S.C § 119 to Japanese Patent Application No. 2019-086597, filed on Apr. 26, 2019, which is hereby expressly incorporated by reference, in its entirety, into the present application.

BACKGROUND

Technical Field

The present disclosure relates to a control device, a radiography system, a medical imaging system, a control method, and a control program.

Related Art

A radiography apparatus has been known which irradiates an object, such as the breast of a subject, with radiation emitted from a radiation source and detects the radiation transmitted through the object with a radiation detector to capture a radiographic image.

In addition, an ultrasonography apparatus has been known which scans the breast of a subject using an ultrasound probe and scans the breast with ultrasonic waves to capture an ultrasound image of the breast.

JP2017-184864A discloses an apparatus that can continuously capture a radiographic image and an ultrasound image of the breast compressed by a compression member. In JP2017-184864A, the radiographic image and the ultrasound image are captured in a state in which the breast is compressed.

In a case in which an ultrasound image is captured and an ultrasound probe for capturing the ultrasound image is a so-called handheld type, the radiation source becomes an obstacle to ultrasonography technology and it may be difficult to capture the ultrasound image.

SUMMARY

The present disclosure has been made in view of the above-mentioned problems and an object of the present disclosure is to provide a control device, a radiography system, a medical imaging system, a control method, and a control program that can facilitate the capture of an ultrasound image.

In order to achieve the above object, according to a first aspect of the present disclosure, there is provided a control device comprising a control unit that, in a case in which continuous imaging that irradiates a breast of a subject with radiation emitted from a radiation source to capture a radiographic image in a compressed state in which the breast is compressed against an imaging table by a compression member and then captures an ultrasound image of the breast in the compressed state is performed, performs control to locate the radiation source at a non-facing position where the radiation source and the imaging table do not face each other.

According to a second aspect of the present disclosure, in the control device according to the first aspect, in a case in which the radiographic image is captured with the radiation source located at the non-facing position, the control unit may perform control to maintain a position of the radiation source at an imaging position where the radiographic image has been captured.

According to a third aspect of the present disclosure, in the control device according to the first aspect, in a case in which the radiographic image is captured with the radiation source located at the non-facing position, the control unit may perform control to set a position of the radiation source as a position where an inclination angle of a radiation axis with respect to an imaging surface is larger than that at an imaging position where the radiographic image has been captured.

According to a fourth aspect of the present disclosure, in the control device according to the second or third aspect, in a case in which a position of an ultrasonography apparatus that captures the ultrasound image and the imaging position are the same on left and right sides of the subject, the control unit may perform control to locate the radiation source at a position that is opposite to the imaging position on the left and right sides of the subject.

According to a fifth aspect of the present disclosure, in the control device according to the fourth aspect, in a case in which the imaging position is a position on the right side of the subject and the position of the ultrasonography apparatus is a position on the right side of the subject, the control unit may perform control to locate the radiation source on the left side of the subject.

According to a sixth aspect of the present disclosure, in the control device according to any one of the first to fifth aspects, the control unit may perform control to locate the radiation source at the non-facing position specified on the basis of correspondence relationship information indicating a correspondence relationship between a type of imaging used to capture the radiographic image and the non-facing position and the type of imaging used to capture the radiographic image.

According to a seventh aspect of the present disclosure, in the control device according to any one of the first to sixth aspects, in a case in which the type of imaging used to capture the radiographic image is medio-lateral oblique imaging, the control unit may perform control to locate the radiation source at a position in a case in which the type of imaging used to capture the radiographic image is cranio-caudal imaging.

According to an eighth aspect of the present disclosure, in the control device according to any one of the first to seventh aspects, in a case in which the type of imaging used to capture the radiographic image is the cranio-caudal imaging, the control unit may perform control to locate the radiation source at a position in a case in which the type of imaging used to capture the radiographic image is the medio-lateral oblique imaging.

According to a ninth aspect of the present disclosure, in the control device according to the eighth aspect, the control unit may perform control to locate the radiation source at a position, which is opposite to the position of the ultrasonography apparatus that captures the ultrasound image on the left and right sides of the subject, among positions in a case in which the medio-lateral oblique imaging is performed.

According to a tenth aspect of the present disclosure, in the control device according to any one of the first to ninth aspects, in a case in which the position of the ultrasonography apparatus that captures the ultrasound image is opposite to the position of the radiation source on the left and right sides of the subject, the control unit may perform control to maintain the position of the radiation source even though the position of the radiation source is a facing position where the radiation source and the imaging table face each other.

Further, in order to achieve the above object, according to an eleventh aspect of the present disclosure, there is provided a control device comprising: a control unit that, in a case in which continuous imaging that irradiates a breast of a subject with radiation emitted from a radiation source to capture a radiographic image in a compressed state in which the breast is compressed against an imaging table by a compression member and then captures an ultrasound image of the breast in the compressed state using an ultrasonography apparatus is performed, performs control to locate the radiation source such that a position of the ultrasonography apparatus and a position of the radiation source are opposite to each other on left and right sides of the subject.

According to a twelfth aspect of the present disclosure, in the control device according to the eleventh aspect, in a case in which the position of the ultrasonography apparatus is a position on the right side of the subject and the position of the radiation source is a position on the right side of the subject, the control unit may perform control to locate the radiation source on the left side of the subject.

According to a thirteenth aspect of the present disclosure, in the control device according to the eleventh or twelfth aspect, in a case in which the position of the ultrasonography apparatus is the position on the left side of the subject and the position of the radiation source is the position on the left side of the subject, the control unit may perform control to locate the radiation source on the right side of the subject.

According to a fourteenth aspect of the present disclosure, the control device according to any one of the fourth aspect and the ninth to thirteenth aspects may further comprise a specification unit that specifies the position of the ultrasonography apparatus. The control unit may set the position of the radiation source as a position corresponding to the position of the ultrasonography apparatus specified by the specification unit.

According to a fifteenth aspect of the present disclosure, the control device according to any one of the first to fourteenth aspects may further comprise an acquisition unit that acquires mammary gland amount information indicating an amount of mammary gland in the breast. The control unit may capture the ultrasound image in a case in which the amount of mammary gland indicated by the mammary gland amount information is equal to or greater than a predetermined amount of mammary gland.

According to a sixteenth aspect of the present disclosure, the control device according to any one of the first to fourteenth aspects may further comprise an acquisition unit that acquires region information indicating a mammary gland region in the breast on the basis of the radiographic image. The control unit may capture the ultrasound image in a case in which a size of the mammary gland region indicated by the region information is equal to or greater than a predetermined size.

In order to achieve the object, according to a seventeenth aspect of the present disclosure, there is provided a radiography system comprising: a mammography apparatus that includes a radiation source, a radiation detector, and a compression member which compresses a breast disposed between the radiation source and the radiation detector and captures a radiographic image of the breast in the compressed state using the radiation detector; and the control device according to any one of the first to sixteenth aspects that controls the mammography apparatus.

In order to achieve the object, according to an eighteenth aspect of the present disclosure, there is provided a medical imaging system comprising: the radiography system according to the seventeenth aspect; and an ultrasonography apparatus that captures an ultrasound image of the breast compressed by the compression member of the mammography apparatus included in the radiography system.

In order to achieve the object, according to a nineteenth aspect of the present disclosure, there is provided a medical imaging system comprising: a medical imaging apparatus that includes a radiation source, a radiation detector, and a compression member which compresses a breast disposed between the radiation source and the radiation detector, captures a radiographic image of the breast in the compressed state using the radiation detector, and captures an ultrasound image of the breast in the compressed state; and the control device according to any one of the first to sixteenth aspects that controls the medical imaging apparatus.

In order to achieve the object, according to a twentieth aspect of the present disclosure, there is provided a control method comprising: in a case in which continuous imaging that irradiates a breast of a subject with radiation emitted from a radiation source to capture a radiographic image in a compressed state in which the breast is compressed against an imaging table by a compression member and then captures an ultrasound image of the breast in the compressed state is performed, performing control to locate the radiation source at a non-facing position where the radiation source and the imaging table do not face each other.

In order to achieve the object, according to a twenty-first aspect of the present disclosure, there is provided a control program that causes a computer to perform: in a case in which continuous imaging that irradiates a breast of a subject with radiation emitted from a radiation source to capture a radiographic image in a compressed state in which the breast is compressed against an imaging table by a compression member and then captures an ultrasound image of the breast in the compressed state is performed, performing control to locate the radiation source at a non-facing position where the radiation source and the imaging table do not face each other.

Further, according to the present disclosure, there is provided a control device including a processor. In a case in which continuous imaging that irradiates a breast of a subject with radiation emitted from a radiation source to capture a radiographic image in a compressed state in which the breast is compressed against an imaging table by a compression member and then captures an ultrasound image of the breast in the compressed state is performed, the processor performs control to locate the radiation source at a non-facing position where the radiation source and the imaging table do not face each other.

According to the present disclosure, it is possible to easily capture an ultrasound image.

BRIEF DESCRIPTION OF THE DRAWINGS

FIG. 4A is a diagram illustrating an example of craniocaudal (CC) imaging performed by the mammography apparatus according to the first embodiment.

FIG. 17 is a diagram illustrating an example of correspondence relationship information according to the third embodiment.

DESCRIPTION OF EMBODIMENTS

Hereinafter, embodiments of the invention will be described in detail with reference to the drawings. Each of the embodiments does not limit the invention. In each of the embodiments, for example, a case in which an object of interest of the present disclosure is the mammary gland will be described.

First Embodiment

Figure 1:
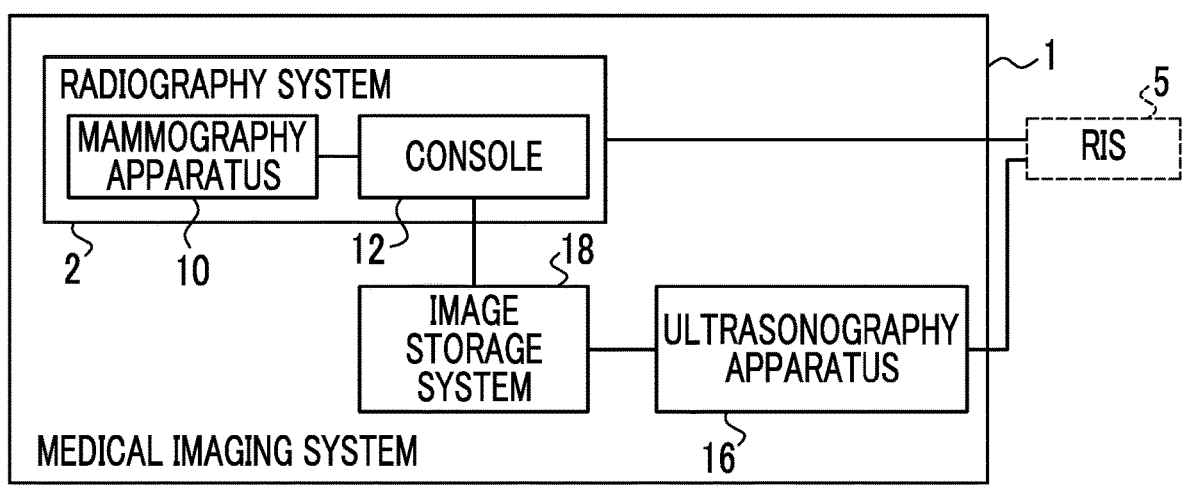
FIG. 1 is a diagram schematically illustrating an example of the overall configuration of a medical imaging system according to a first embodiment.

First, an example of the overall configuration of a medical imaging system according to this embodiment will be described. FIG. 1 is a diagram illustrating an example of the overall configuration of a medical imaging system 1 according to this embodiment.

As illustrated in FIG. 1, the medical imaging system 1 according to this embodiment comprises a radiography system 2, an ultrasonography apparatus 16, and an image storage system 18.

Figure 2:
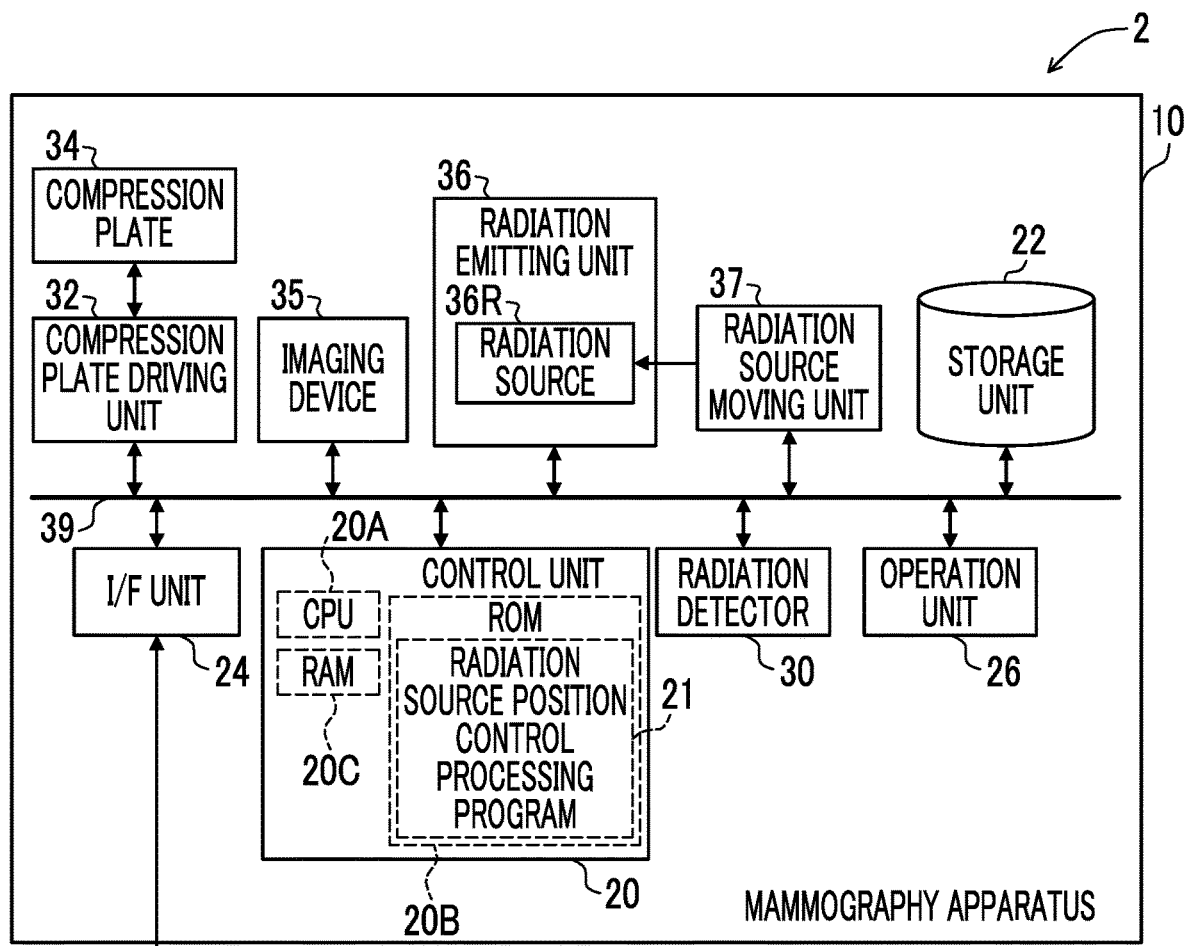
FIG. 2 is a block diagram illustrating an example of the configuration of a console and a mammography apparatus according to the first embodiment.
Figure 2:
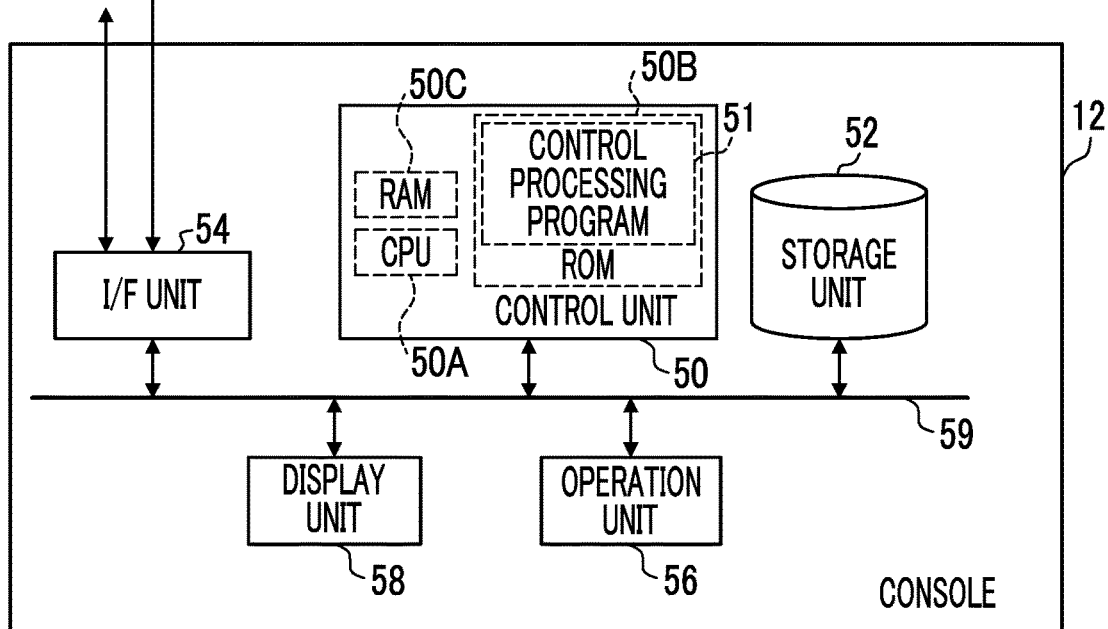
Figure 3:
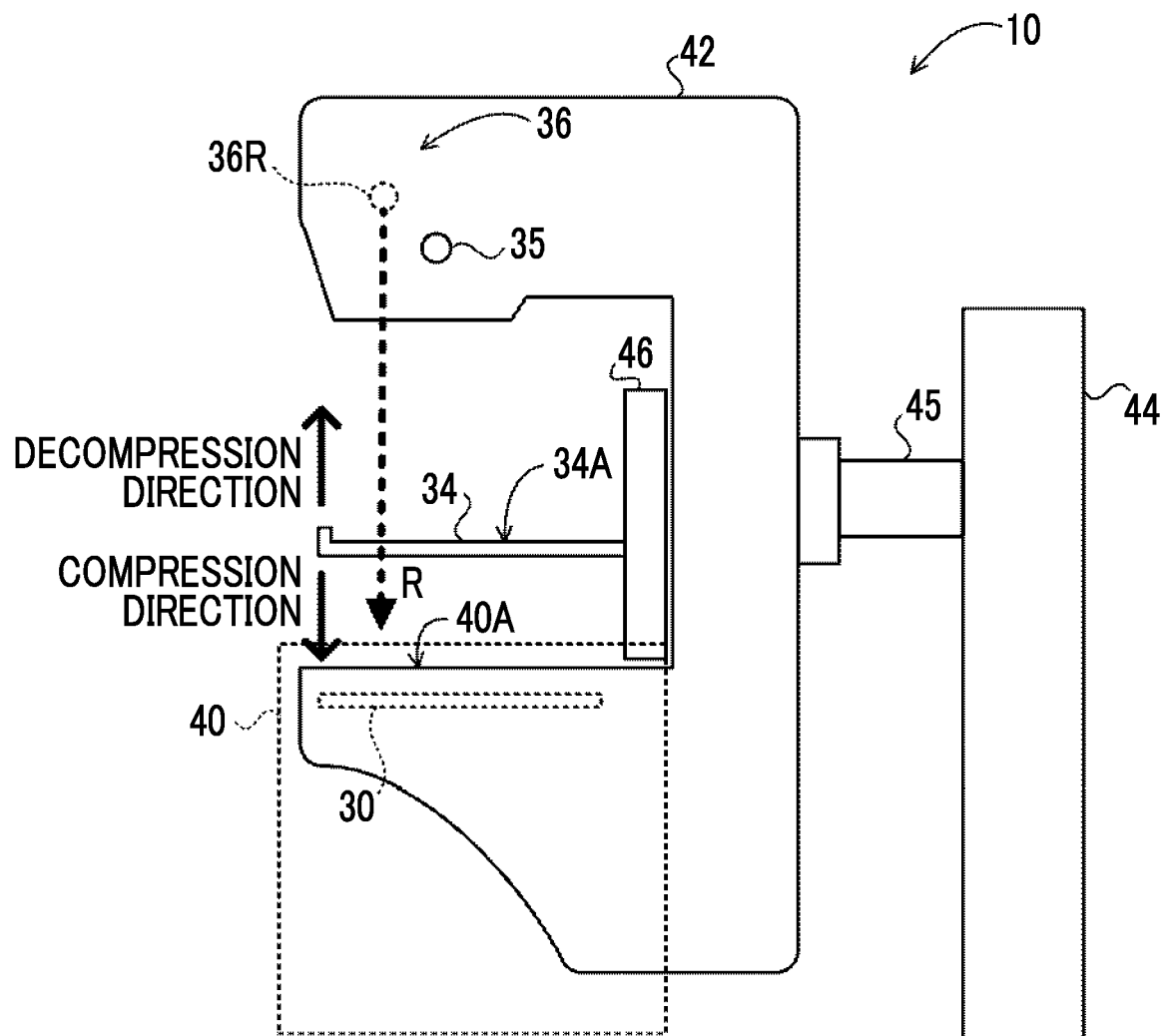
FIG. 3 is a side view illustrating an example of the outward appearance of the mammography apparatus according to the first embodiment.
Figure 3:
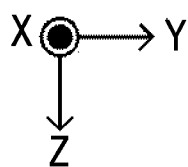

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the outward appearance of the mammography apparatus 10 according to this embodiment. FIG. 3 illustrates an example of the outward appearance of the mammography apparatus 10 as viewed from the right side of a subject.

The mammography apparatus 10 according to this embodiment irradiates the breast of the subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, an interface (I/F) unit 24, an operation unit 26, a radiation detector 30, a compression plate driving unit 32, a compression plate 34, an imaging device 35, a radiation emitting unit 36, and a radiation source moving unit 37. The control unit 20, the storage unit 22, the I/F unit 24, the operation unit 26, the radiation detector 30, the compression plate driving unit 32, the imaging device 35, the radiation emitting unit 36, and the radiation source moving unit 37 are connected to each other through a bus 39, such as a system bus or a control bus, such that they can transmit and receive various kinds of information.

The control unit 20 according to this embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including a radiation source position control processing program 21 which is executed by the CPU 20A and performs control related to the capture of a radiographic image are stored in the ROM 20B in advance. The RAM 20C temporarily stores various kinds of data.

The radiation detector 30 detects the radiation R transmitted through the breast which is the object. As illustrated in FIG. 3, the radiation detector 30 is provided in an imaging table 40. In the mammography apparatus 10 according to this embodiment, in a case in which imaging is performed, the breast of the subject is positioned on an imaging surface 40A of the imaging table 40 by a user such as a doctor or a radiology technician. For example, the imaging surface 40A with which the breast of the subject comes into contact is made of carbon in terms of the transmission and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

For example, the image data of the radiographic image captured by the radiation detector 30 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 30 in the mammography apparatus 10 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a radiation source 36R. As illustrated in FIG. 3, the radiation emitting unit 36 is provided in an arm portion 42 together with the imaging table 40 and a compression unit 46. In addition, as illustrated in FIG. 3, the mammography apparatus 10 according to this embodiment comprises the arm portion 42, a base 44, and a shaft portion 45. The arm portion 42 is supported by the base 44 so as to be movable in the up-down direction (Z-axis direction). The shaft portion 45 connects the arm portion 42 to the base 44. The radiation source moving unit 37 can relatively rotate the arm portion 42 with respect to the base 44, using the shaft portion 45 as a rotation axis.

In the mammography apparatus 10 according to this embodiment, at least two types of imaging can be performed to capture radiographic images. Specifically, the mammography apparatus 10 performs at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 36R in a case in which the radiation R is emitted from the radiation source 36R to the imaging table 40 in the capture of a radiographic image is referred to as an "imaging position".

In a case in which the CC imaging is performed, as illustrated in FIG. 4A, the imaging table 40 is adjusted to a state in which the imaging surface 40A faces the upper side of the mammography apparatus 10 (the head of the subject), that is, a state in which a normal line CL to the imaging surface 40A is perpendicular to a floor surface. In this case, the position of the radiation source 36R is adjusted to an imaging position that faces the imaging surface 40A of the imaging table 40. Therefore, the radiation R is emitted from the radiation source 36R to the breast in a direction from the head to the foot of the subject and the CC imaging is performed.

Figure 4B:
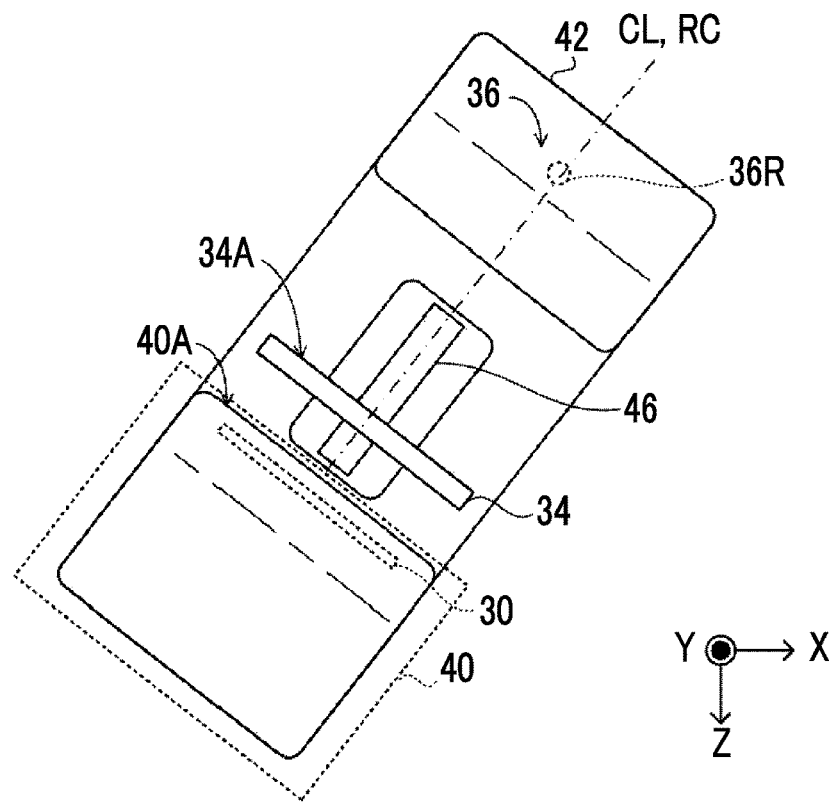
FIG. 4B is a diagram illustrating an example of mediolateral oblique (MLO) imaging for the left breast of a subject performed by the mammography apparatus according to the first embodiment.
Figure 4C:
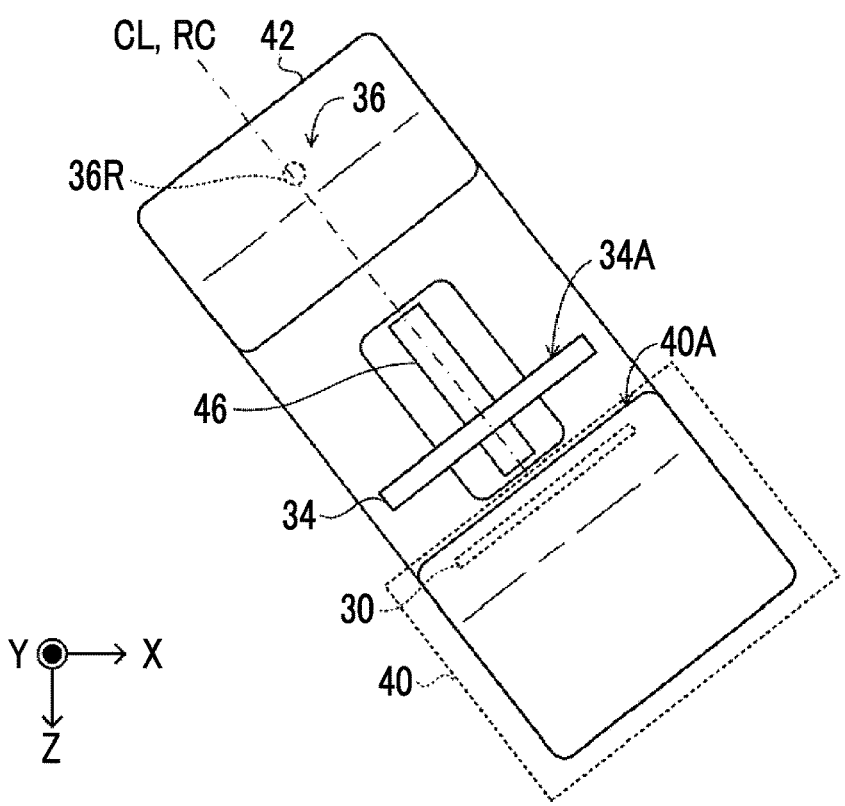
FIG. 4C is a diagram illustrating an example of the MLO imaging for the right breast of the subject performed by the mammography apparatus according to the first embodiment.

In contrast, in a case in which the MLO imaging is performed, as illustrated in FIGS. 4B and 4C, the position of the imaging table 40 is adjusted to a state in which the imaging surface 40A is rotated up to a predetermined angle in a range of, for example, 45 degrees or more and less than 90 degrees with respect to the case in which the CC imaging is performed. Specifically, in a case in which an image of the left breast of the subject is captured, for example, the arm portion 42 is inclined such that the imaging surface 40A is inclined to the right as illustrated in FIG. 4B. Therefore, in a case in which the MLO imaging is performed for the left breast of the subject, the radiation source 36R is inclined to the right of the subject. In addition, in a case in which an image of the right breast of the subject is captured, as illustrated in FIG. 4C, the arm portion 42 is inclined such that the imaging surface 40A is inclined to the left. Therefore, in a case in which the MLO imaging is performed for the right breast of the subject, the radiation source 36R is inclined to the left of the subject. Therefore, the radiation R is emitted from the radiation source 36R to the breast in a direction from the center of the body of the subject to the outside (in a direction from a space between the breasts of the subject to the arm) and the MLO imaging is performed.

As described above, in the mammography apparatus 10 according to this embodiment, in both the CC imaging and the MLO imaging, the radiation source 36R and the imaging surface 40A of the imaging table 40 face each other at the imaging position.

The compression plate driving unit 32 and the compression plate 34 are provided in the compression unit 46. Each of the compression unit 46 and the arm portion 42 can be relatively rotated with respect to the base 44, using the shaft portion 45 as a rotation axis. In this embodiment, gears (not illustrated) are provided in each of the shaft portion 45, the arm portion 42, and the compression unit 46. Each gear is switched between an engaged state and a disengaged state to connect each of the arm portion 42 and the compression unit 46 to the shaft portion 45. One or both of the arm portion 42 and the compression unit 46 connected to the shaft portion 45 are rotated integrally with the shaft portion 45.

The compression plate 34 according to this embodiment is a plate-shaped compression member and is moved in the up-down direction (Z-axis direction) by the compression plate driving unit 32 to compress the breast of the subject against the imaging table 40. As illustrated in FIG. 3, for the movement direction of the compression plate 34, the direction in which the breast is compressed, that is, the direction in which the compression plate 34 becomes closer to the imaging surface 40A is referred to as a "compression direction" and the direction in which the compression of the breast is released, that is, the direction in which the compression plate 34 becomes closer to the radiation emitting unit 36 is referred to as a "decompression direction".

It is preferable that the compression plate 34 is optically transparent in order to check positioning or a compressed state in the compression of the breast. In addition, the compression plate 34 is made of a material having high transmittance for the radiation R. It is desirable that the compression plate 34 is made of a material that facilitates the transmission of ultrasonic waves from an ultrasound probe 65 (see FIG. 7, which will be described in detail below) of the ultrasonography apparatus 16. Examples of the material forming the compression plate 34 include resins such as polymethylpentene, polycarbonate, acrylic, and polyethylene terephthalate. In particular, polymethylpentene is suitable as the material forming the compression plate 34 since it has low rigidity, high elasticity, and high flexibility and has suitable values for acoustic impedance that affects the reflectance of ultrasonic waves and an attenuation coefficient that affects the attenuation of ultrasonic waves. The member forming the compression plate 34 is not limited to this embodiment. For example, the member forming the compression plate 34 may be a film-like member.

In this example, the compression plate 34 compresses the entire breast. However, the present disclosure is not limited thereto. The compression plate 34 may compress a part of the breast. In other words, the compression plate 34 may be smaller than the breast. For example, a compression plate 34 used for so-called spot imaging which captures a radiographic image of only a region in which a lesion exists is known as the compression plate 34.

The imaging device 35 is, for example, a camera that is provided in the arm portion 42 of the mammography apparatus 10, captures an image of the surroundings of the mammography apparatus 10, and outputs the captured image, as illustrated in FIG. 3. Specifically, the imaging device 35 is provided on a side surface of the arm portion 42 in the vicinity of the radiation emitting unit 36 and captures the image of the surroundings on the right and left sides of the subject. The number of imaging devices 35 is not limited to one and may be two or more.

In this embodiment, the imaging device 35 is provided in the mammography apparatus 10. However, the imaging device 35 may be provided in an apparatus other than the mammography apparatus 10. For example, the console 12 may comprise the imaging device 35. In addition, for example, a single imaging device 35 may be disposed in an imaging room in which the mammography apparatus 10 is disposed.

Figure 5:
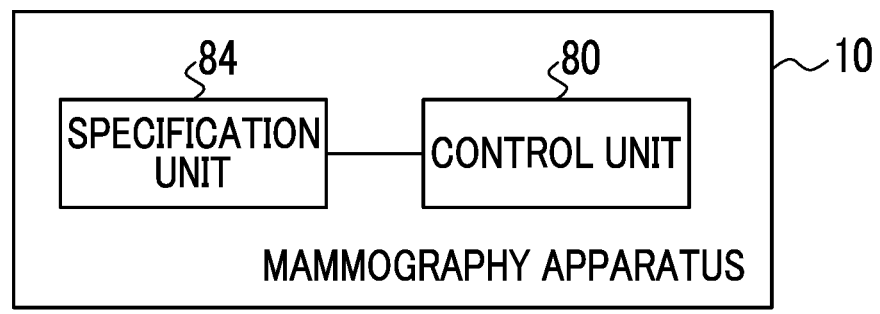
FIG. 5 is a functional block diagram illustrating an example of the function of a mammography apparatus according to the first embodiment.

FIG. 5 is a functional block diagram illustrating an example of the configuration of the mammography apparatus 10 according to this embodiment. As illustrated in FIG. 5, the mammography apparatus 10 according to this embodiment comprises a control unit 80 and a specification unit 84. For example, in the mammography apparatus 10 according to this embodiment, the CPU 20A of the control unit 20 executes the radiation source position control processing program 21 stored in the ROM 20B such that the control unit 20 functions as the control unit 80 and the specification unit 84. The mammography apparatus 10 according to this embodiment is an example of a control device according to the present disclosure.

The specification unit 84 of the mammography apparatus 10 specifies the position of the ultrasonography apparatus 16 from the image captured by the imaging device 35 and outputs radiation source position information indicating the position of the ultrasonography apparatus 16 to the control unit 80.

For example, in this embodiment, the positions of the ultrasonography apparatus 16 and the radiation source 36R are specified on the basis of the position of the subject. Therefore, the specification unit 84 according to this embodiment specifies the position of the ultrasonography apparatus 16 on the basis of the position of the subject. Specifically, the specification unit 84 specifies whether the ultrasonography apparatus 16 is located on the right side of the subject or on the left side of the subject.

Therefore, the specification unit 84 specifies whether the position of the ultrasonography apparatus 16 is a position on the left side or a position on the right side of the subject from the image captured by the imaging device 35 and outputs information indicating whether the position is on the left side or on the right side of the subject as the radiation source position information to the control unit 80. A method for specifying the position of the ultrasonography apparatus 16 from the image captured by the imaging device 35 is not particularly limited. For example, the position of the ultrasonography apparatus 16 may be specified by applying an existing image analysis technique to the captured image to detect an image indicating the subject and an image indicating the ultrasonography apparatus 16 and specifying the left and right positions of the two images.

As described above, the specification unit 84 according to this embodiment specifies the position of the ultrasonography apparatus 16 from the image captured by the imaging device 35. However, the method for specifying the position of the ultrasonography apparatus 16 in the specification unit 84 is not limited to this embodiment. For example, the following configuration may be used: the user inputs information indicating the position of the ultrasonography apparatus 16 through the operation unit 26 and the specification unit 84 specifies the position of the ultrasonography apparatus 16 on the basis of the information indicating the position of the ultrasonography apparatus 16 input by the user. Further, for example, in a case in which the position of the ultrasonography apparatus 16 is set in advance in the mammography apparatus 10, the set position of the ultrasonography apparatus 16 may be acquired and the specification unit 84 may specify the position of the ultrasonography apparatus 16.

In addition, the radiation source position information is input from the specification unit 84 to the control unit 80. In a case in which continuous imaging that captures a radiographic image and then captures an ultrasound image in a compressed state in which the breast is compressed by the compression plate 34 is performed, the control unit 80 performs control to set the position of the radiation source 36R in the capture of the ultrasound image as a retreat position.

Figure 6:
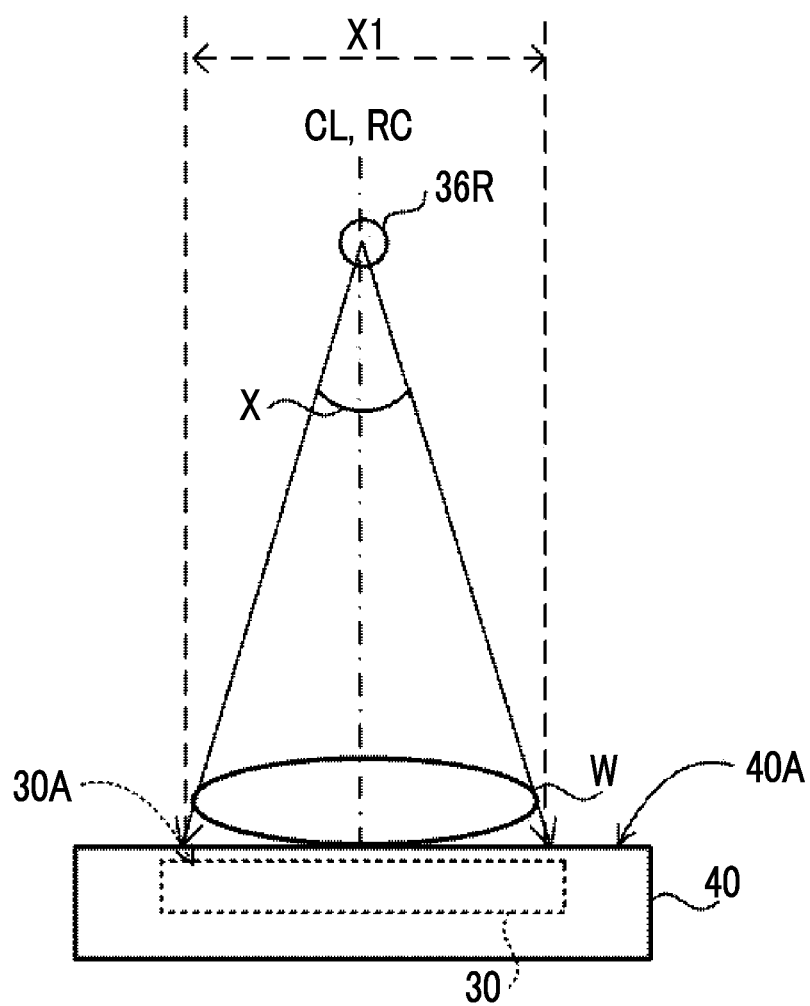
FIG. 6 is a diagram illustrating a non-facing position.

The retreat position is a position where the radiation source 36R does not hinder the user who operates an ultrasound probe 65 of the ultrasonography apparatus 16. Generally, in a case in which an ultrasound image is captured, the ultrasound probe 65 is moved along an upper surface 34A of the compression plate 34 by the operation of the user, which will be described below. Therefore, in a case in which the radiation source 36R is located at a position facing the upper surface 34A of the compression plate 34, the radiation source 36R is likely to hinder the user. In other words, in a case in which the position of the radiation source 36R is a facing position that faces the imaging table 40, the radiation source 36R is likely to hinder the user who takes an ultrasound image. The "facing position" where the radiation source 36R and the imaging table 40 face each other is a position where a radiation axis RC of the radiation source 36R is perpendicular to the imaging table 40 (imaging surface 40A). On the other hand, a "non-facing position" where the radiation source 36R and the imaging table 40 do not face each other is referred to as a position where the radiation axis RC of the radiation source 36R is inclined with respect to the imaging table 40 (imaging surface 40A). In other words, the position where the normal line CL to the imaging surface 40A of the imaging table 40 is aligned with the radiation axis RC is referred to as the "facing position" and the position where the normal line CL is not aligned with the radiation axis RC is referred to as the "non-facing position". As illustrated in FIG. 6, the "non-facing position" may be a position within a range X1 corresponding to an irradiation field X of the radiation source 36R in a case in which the radiation axis RC of the radiation source 36R and the normal line CL are aligned with each other.

Therefore, in this embodiment, the position where the radiation source 36R does not hinder the user who takes an ultrasound image as described above is determined as the retreat position in advance. For example, in this embodiment, in a case in which the capture of a radiographic image in the continuous imaging is the CC imaging, the position of the radiation source 36R in the MLO imaging is set as the retreat position. In a case in which the capture of a radiographic image in the continuous imaging is the MLO imaging, the position of the radiation source 36R in the CC radiography is set as the retreat position. As described above, in the mammography apparatus 10 according to this embodiment, the non-facing position where the radiation source 36R and the imaging table 40 do not face each other is set as the retreat position.

In a case in which the continuous imaging is performed, the compressed state of the breast may not be completely the same between the state in which the radiographic image is captured and the state in which the ultrasound image is captured. For example, the compression force or compression pressure of the compression plate 34 against the breast may be changed. As described above, the overlap of the mammary gland tissues is developed by the compression of the breast by the compression plate 34. Therefore, it is possible to change the compression force or the compression pressure to the extent that the overlap of the mammary gland tissues, that is, the development of the mammary gland tissues is not changed or the amount of change is within an allowable range even in a case in which the overlap is changed. For example, as the compressed state of the breast for the time from the start of the capture of a radiographic image to the end of the capture of an ultrasound image, the breast may be continuously compressed to the extent that the area of the breast which comes into contact with the imaging surface 40A of the imaging table 40 is not changed. Therefore, the mammography apparatus 10 may reduce the compression against the breast according to the area of the breast which comes into contact with the imaging surface 40A after a radiographic image is captured and before an ultrasound image is captured.

Further, in a case in which the user inputs a command to move the radiation source 36R using the operation unit 26, the control unit 80 according to this embodiment performs control to move the radiation source 36R to a position corresponding to the command.

The console 12 according to this embodiment has a function of controlling the mammography apparatus 10 using, for example, an imaging order and various kinds of information acquired from a radiology information system (RIS) 5 through a wireless communication local area network (LAN) and commands input by the user through an operation unit 56.

For example, the console 12 according to this embodiment is a server computer. As illustrated in FIG. 2, the console 12 comprises a control unit 50, a storage unit 52, an I/F unit 54, the operation unit 56, and a display unit 58. The control unit 50, the storage unit 52, the I/F unit 54, operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a control processing program 51 (which will be described below) executed by the CPU 50A are stored in the ROM 50B in advance. The RAM 50C temporarily stores various kinds of data.

For example, the image data of the radiographic image captured by the mammography apparatus 10 and various other kinds of information are stored in the storage unit 52. An HDD or an SSD is given as an example of the storage unit 52.

The operation unit 56 is used by the user to input, for example, commands which are related to the capture of a radiographic image and include a command to emit the radiation R or various kinds of information. Therefore, the operation unit 56 according to this embodiment includes at least an irradiation command button that is pressed by the user to input a command to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS 5, and the image storage system 18 using wireless communication or wired communication. In the radiography system 2 according to this embodiment, the console 12 receives the image data of the radiographic image captured by the mammography apparatus 10 from the mammography apparatus 10 through the I/F unit 54, using wireless communication or wired communication.

Figure 7:
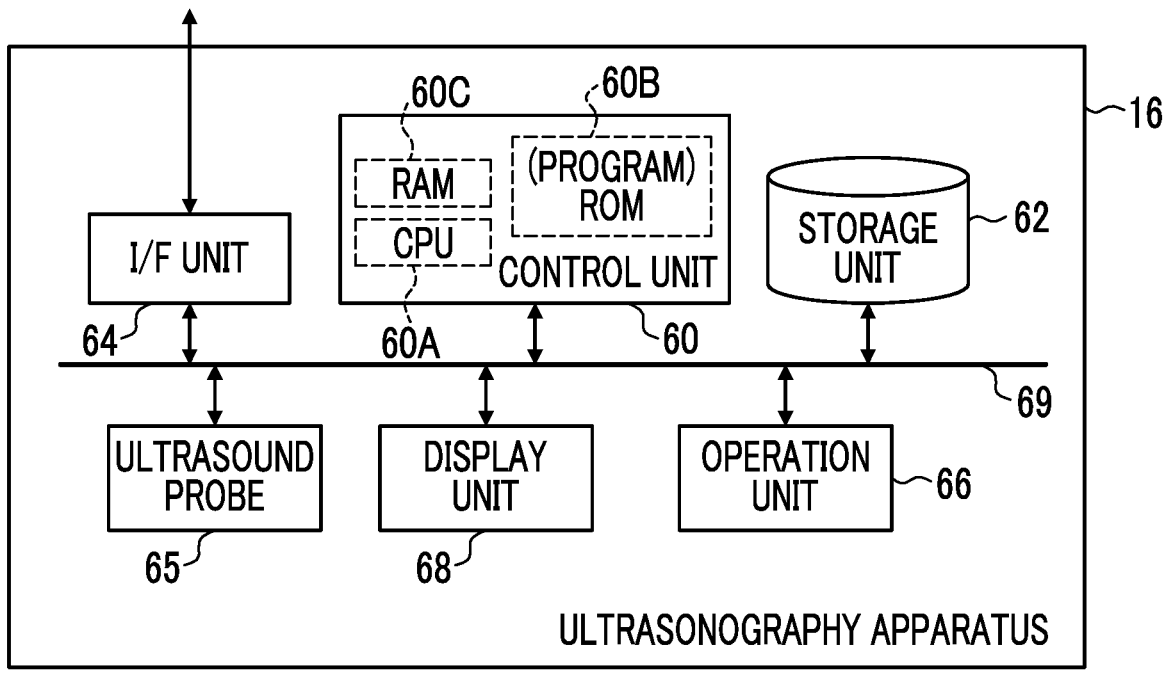
FIG. 7 is a block diagram illustrating an example of the configuration of an ultrasonography apparatus according to the first embodiment.

Next, the configuration of the ultrasonography apparatus 16 will be described. FIG. 7 is a block diagram illustrating an example of the configuration of the ultrasonography apparatus 16. The ultrasonography apparatus 16 is used by the user to capture an ultrasound image of the breast of the subject as the object and is a so-called hand-held ultrasonography apparatus.

As illustrated in FIG. 7, the ultrasonography apparatus 16 comprises a control unit 60, a storage unit 62, an I/F unit 64, the ultrasound probe 65, an operation unit 66, and a display unit 68. The control unit 60, the storage unit 62, the I/F unit 64, the ultrasound probe 65, the operation unit 66, and the display unit 68 are connected to each other through a bus 69, such as a system bus or a control bus, such that they can transmit and receive various kinds of information.

The control unit 60 according to this embodiment controls the overall operation of the ultrasonography apparatus 16. The control unit 60 comprises a CPU 60A, a ROM 60B, and a RAM 60C. For example, various programs executed by the CPU 60A are stored in the ROM 60B in advance. The RAM 60C temporarily stores various kinds of data.

For example, the image data of the captured ultrasound image and various other kinds of information are stored in the storage unit 62. A specific example of the storage unit 62 is an HDD or an SSD.

The ultrasound probe 65 is moved along the upper surface 34A (see FIG. 3, a surface opposite to the surface that comes into contact with the breast of the subject) of the compression plate 34 by the user and scans the breast with ultrasonic waves to acquire an ultrasound image of the breast. Specifically, in a case in which ultrasonography is performed, the ultrasound probe 65 is moved by the user along the upper surface 34A of the compression plate 34 in a state in which an acoustic matching member (not illustrated), such as echo jelly, is applied onto the upper surface 34A of the compression plate 34.

The ultrasound probe 65 comprises a plurality of ultrasound transducers (not illustrated) which are one-dimensionally or two-dimensionally arranged. Each of the ultrasound transducers transmits ultrasonic waves on the basis of an applied driving signal, receives ultrasound echoes, and outputs a received signal.

For example, each of the plurality of ultrasound transducers is a transducer configured by forming electrodes at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are combined to form an ultrasound beam. Each transducer receives the propagated ultrasonic waves and is then expanded and contracted to generate an electric signal. The electric signal is output as an ultrasound received signal and is input to the main body (not illustrated) of the ultrasonography apparatus 16 through a cable (not illustrated).

The operation unit 66 is used by the user to input, for example, commands or various kinds of information related to the capture of an ultrasound image. The operation unit 66 is not particularly limited. Examples of the operation unit 66 include various switches, a touch panel, a touch pen, and a mouse. The display unit 68 displays, for example, various kinds of information or an ultrasound image corresponding to the received signal from the ultrasound probe 65. In addition, the operation unit 66 and the display unit 68 may be integrated into a touch panel display.

The I/F unit 64 transmits and receives various kinds of information to and from the RIS 5 and the image storage system 18 using wireless communication or wired communication. The image data of the ultrasound image captured by the ultrasonography apparatus 16 is transmitted to the image storage system 18 through the I/F unit 64 by wireless communication or wired communication.

Figure 8:
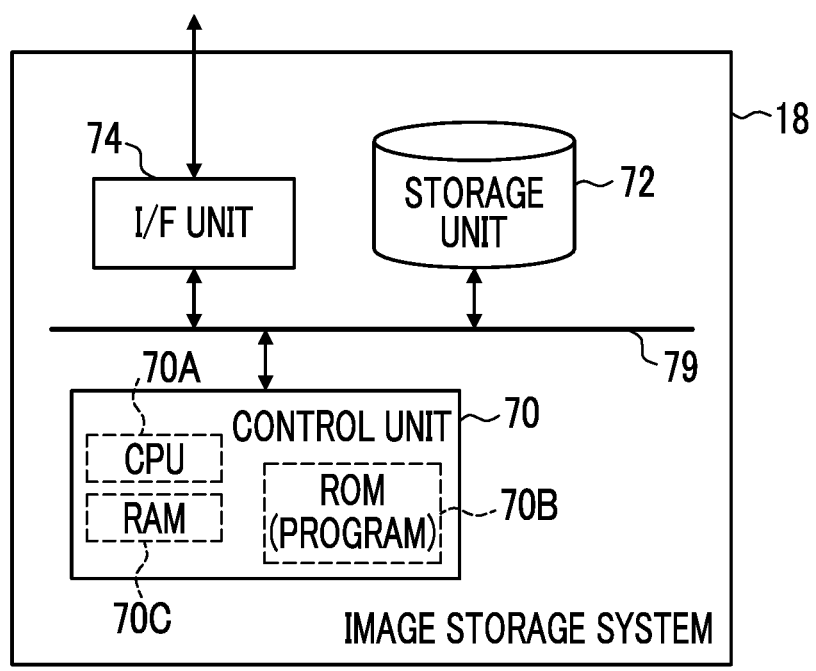
FIG. 8 is a block diagram illustrating an example of the configuration of an image storage system according to the first embodiment.

Next, the configuration of the image storage system 18 will be described. FIG. 8 is a block diagram illustrating an example of the configuration of the image storage system 18. The image storage system 18 stores the image data of the radiographic image captured by the radiography system 2 and the image data of the ultrasound image captured by the ultrasonography apparatus 16. The image storage system 18 extracts an image corresponding to a request from, for example, the console 12, the ultrasonography apparatus 16, and other reading devices (not illustrated) from the stored radiographic images and ultrasound images and transmits the extracted image to the apparatus which is the request source. A specific example of the image storage system 18 is a picture archiving and communication system (PACS).

As illustrated in FIG. 8, the image storage system 18 comprises a control unit 70, a storage unit 72, and an I/F unit 74. The control unit 70, the storage unit 72, and the I/F unit 74 are connected to each other through a bus 79, such as a system bus or a control bus, such that they can transmit and receive various kinds of information.

The control unit 70 according to this embodiment controls the overall operation of the ultrasonography apparatus 16. The control unit 70 comprises a CPU 70A, a ROM 70B, and a RAM 70C. For example, various programs executed by the CPU 70A are stored in the ROM 70B in advance. The RAM 70C temporarily stores various kinds of data.

The storage unit 72 is a so-called database that stores each of the image data of the radiographic image and the image data of the ultrasound image so as to be associated with, for example, an imaging order or information released to the subject.

The I/F unit 74 has a function of transmitting and receiving various kinds of information to and from the console 12 and the ultrasonography apparatus 16 using wireless communication or wired communication.

Figure 9:
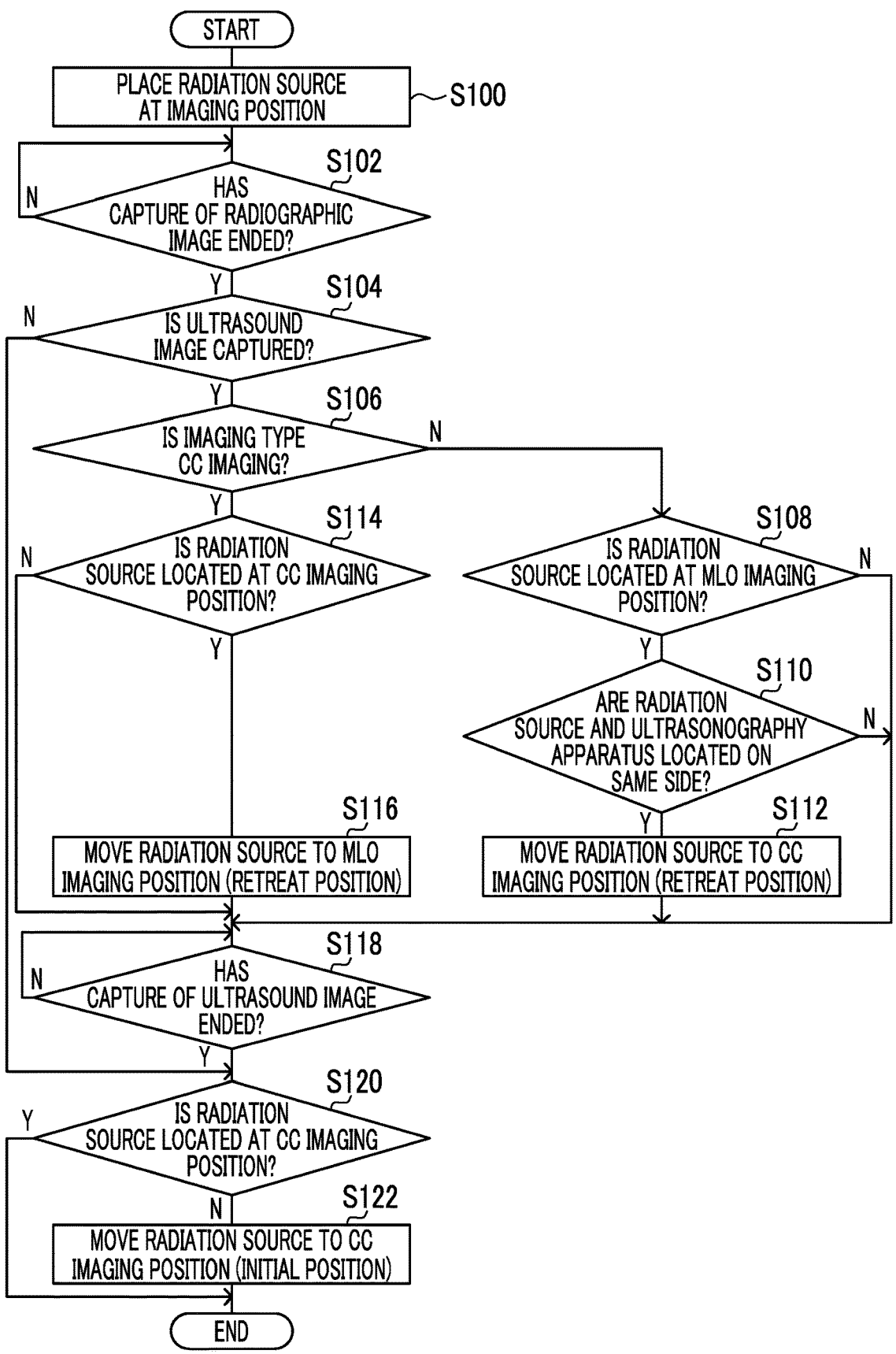
FIG. 9 is a flowchart illustrating an example of the flow of a radiation source position control process of the mammography apparatus according to the first embodiment.

Next, the operation of the mammography apparatus 10 according to this embodiment will be described with reference to the drawings. For example, in a case in which the mammography apparatus 10 according to this embodiment receives an imaging order and an imaging start command from the console 12, the CPU 20A of the control unit 20 executes the radiation source position control processing program 21 stored in the ROM 20B to perform a radiation source position control process whose example is illustrated in FIG. 9. FIG. 9 is a flowchart illustrating an example of the flow of a radiation source position control operation of the mammography apparatus 10 according to this embodiment.

First, in Step S100, the control unit 80 places the radiation source 36R at an imaging position corresponding to the type of imaging used to capture the radiographic image. Specifically, the control unit 80 places the radiation source 36R at an imaging position (see FIGS. 4A to 4C) in one of the CC imaging, MLO imaging for the left chest of the subject, and MLO imaging for the right chest of the subject according to an imaging menu. In a case in which the radiation source 36R is moved, the control unit 80 integrally moves the radiation source 36R and the imaging table 40. In other words, the control unit 80 moves the radiation source 36R while maintaining the positional relationship in which the radiation source 36R faces the imaging table 40.

In a case in which the imaging table 40 and the radiation source 36R of the mammography apparatus 10 are located at the imaging position, the user positions the breast of the subject on the imaging surface 40A of the imaging table 40. In a case in which the positioning is completed, the user inputs a compression command through the operation unit 26. In response to the compression command, the compression plate driving unit 32 moves the compression plate 34 in the compression direction and the compression plate 34 compresses the breast between the compression plate 34 and the imaging surface 40A of the imaging table 40.

The compression of the breast by the compression plate 34 makes it possible to develop the overlap between the mammary gland tissues and to easily determine whether a lesion is a benign lesion or a malignant lesion. In addition, since the breast is compressed and fixed to the imaging table 40 by the compression plate 34, the body movement of the subject is suppressed. Therefore, it is possible to suppress the blurring of a radiographic image caused by the body movement. Further, since the breast is compressed by the compression plate 34, the thickness of the breast is reduced. Therefore, it is possible to reduce the amount of radiation emitted to the breast.

In a case in which the breast is fixed by the compression plate 34, the user presses an irradiation command button included in the operation unit 56 of the console 12 to input a command to emit the radiation R. In a case in which the irradiation command is input, the control unit 20 of the mammography apparatus 10 performs control such that the radiation R is emitted from the radiation source 36R to the breast compressed by the compression plate 34 under the control of the console 12. Then, the radiation detector 30 generates a radiographic image on the basis of the radiation R transmitted through the breast. The image data of the captured radiographic image is transmitted to the console 12.

Then, in Step S102, the control unit 80 determines whether the capture of a radiographic image has ended. For example, in a case in which the image data indicating the radiographic image captured by the radiation detector 30 has been transmitted to the console 12, the control unit 80 according to this embodiment determines that the capture of a radiographic image has ended. A method for determining whether the capture of a radiographic image has ended is not limited to this embodiment. For example, a command to end the capture of a radiographic image which has been input through the operation unit 56 of the console 12 may be received.

Until the capture of a radiographic image ends, the determination result in Step S102 is "No". On the other hand, in a case in which the capture of a radiographic image ends, the determination result in Step S102 is "Yes" and the process proceeds to Step S104.

In Step S104, the control unit 80 determines whether or not to capture an ultrasound image. In other words, the control unit 80 determines whether or not to perform the continuous imaging. For example, in a case in which a command to capture both a radiographic image and an ultrasound image is included in the imaging order or the user inputs a command to capture an ultrasound image through the operation unit 56, the control unit 80 according to this embodiment determines to capture an ultrasound image.

In a case in which an ultrasound image is not captured, the determination result in Step S104 is "No" and the process proceeds to Step S120. On the other hand, in a case in which an ultrasound image is captured, the determination result in Step S104 is "Yes" and the process proceeds to Step S106.

In Step S106, the control unit 80 determines whether or not the type of imaging used to capture the radiographic image which has been performed first is the CC imaging. In a case in which the type of imaging is not the CC imaging, that is, in a case in which the type of imaging is the MLO imaging, the determination result in Step S106 is "No" and the process proceeds to Step S108. On the other hand, in a case in which the type of imaging is the CC imaging, the determination result in Step S106 is "Yes" and the process proceeds to Step S114.

In a case in which the type of imaging is the MLO imaging, in Step S108, the control unit 80 determines whether or not the current position of the radiation source 36R is an imaging position for the MLO imaging. In a case in which the user inputs a command to move the radiation source 36R through the operation unit 26 after the end of the MLO imaging, the current position of the radiation source 36R may be different from the imaging position for the MLO imaging. In this case, the radiation source 36R and the imaging table 40 are at the non-facing position where they do not face each other.

In a case in which the current position of the radiation source 36R is not the imaging position for MLO imaging, the determination result in Step S108 is "No" and the process proceeds to Step S118. On the other hand, in a case in which the current position of the radiation source 36R is the imaging position for MLO imaging, the determination result in Step S108 is "Yes" and the process proceeds to Step S110.

In Step S110, the control unit 80 determines whether or not the radiation source 36R and the ultrasonography apparatus 16 are located on the same side. Specifically, the control unit 80 determines whether both the radiation source 36R and the ultrasonography apparatus 16 are on the right side of the subject or whether both the radiation source 36R and the ultrasonography apparatus 16 are on the left side of the subject, on the basis of the radiation source position information input from the specification unit 84.

The case in which the radiation source 36R and the ultrasonography apparatus 16 are not on the same side is a case in which the radiation source 36R is located on the right side of the subject as illustrated in FIG. 4B and the ultrasonography apparatus 16 is located on the left side of the subject and a case in which the radiation source 36R is located on the left side of the subject as illustrated in FIG. 4C and the ultrasonography apparatus 16 is located on the right side of the subject. In this case, the radiation source 36R does not often hinder the user who takes an ultrasound image. Therefore, the control unit 80 according to this embodiment determines that the radiation source 36R and the imaging table 40 are located at the facing position where they face each other and the radiation source 36R is located at the retreat position. Therefore, in this embodiment, in a case in which the radiation source 36R and the ultrasonography apparatus 16 are not on the same side, the determination result in Step S110 is "No" and the process proceeds to Step S118.

On the other hand, in a case in which the radiation source 36R and the ultrasonography apparatus 16 are on the same side, the determination result in Step S110 is "Yes" and the process proceeds to Step S112. In Step S112, the control unit 80 directs the radiation source moving unit 37 to move the radiation source 36R to the imaging position for CC imaging, which is the retreat position in a case in which the type of imaging is the MLO imaging, and then proceeds to Step S118.

On the other hand, in a case in which the type of imaging is the CC imaging, in Step S114, the control unit 80 determines whether or not the current position of the radiation source 36R is the imaging position for CC imaging. In a case in which the user inputs a command to move the radiation source 36R through the operation unit 26 after the end of the CC imaging, the current position of the radiation source 36R may be different from the imaging position for CC imaging. In this case, the radiation source 36R and the imaging table 40 are at the non-facing position where they do not face each other.

In a case in which the current position of the radiation source 36R is not the imaging position for CC imaging, the determination result in Step S114 is "No" and the process proceeds to Step S118. On the other hand, in a case in which the current position of the radiation source 36R is the imaging position for CC imaging, the determination result in Step S114 is "Yes" and the process proceeds to Step S116.

In Step S116, the control unit 80 directs the radiation source moving unit 37 to move the radiation source 36R to the imaging position for MLO imaging, which is the retreat position in a case in which the type of imaging is the CC imaging, and then proceeds to Step S118. In this case, the retreat position may be any of the imaging position (see FIG. 4B) for MLO imaging in a case in which the image of the left breast of the subject is captured or the imaging position (see FIG. 4C) for MLO imaging in a case in which the image of the right breast of the subject is captured. As described above, in a case in which the radiation source 36R and the ultrasonography apparatus 16 are on the same side, the radiation source 36R may be a hindrance. Therefore, it is preferable to set the imaging position for MLO imaging which is opposite to the ultrasonography apparatus 16 on the left and right sides of the subject as the retreat position.

In a case in which the radiation source 36R is moved to the retreat position as in Step S116 and Step S112, it is preferable that the control unit 80 displays, on the display unit 58, information indicating that the capture of an ultrasound image may be started after the radiation source 36R is moved. Alternatively, it is preferable that the control unit 80 notifies the user that the radiation source 36R is moved before the movement of the radiation source 36R is started. In a case in which the radiation source 36R is moved in a state in which the subject is in the vicinity of the mammography apparatus 10, there is a concern that the radiation source 36R will come into contact with the user. As described above, it is preferable to present the timing when an ultrasound image is captured or to notify that the radiation source 36R is moved. In this case, it is possible to prevent the user from approaching the mammography apparatus 10. In addition, from the same point of view, it is preferable that the control unit 80 moves the radiation source 36R in a case in which it is detected that there is no user in the vicinity of the mammography apparatus 10.

The user operates the ultrasonography apparatus 16 to capture an ultrasound image of the breast. Specifically, the user applies an acoustic matching member (not illustrated), such as echo jelly, onto the upper surface 34A of the compression plate 34. The user operates the ultrasound probe 65 to scan the upper surface 34A of the compression plate 34 covered by the acoustic matching member with ultrasonic waves, thereby capturing an ultrasound image. The captured ultrasound image is displayed on the display unit 68 of the ultrasonography apparatus 16.

Then, in Step S118, the control unit 80 determines whether the capture of an ultrasound image has ended. For example, in the medical imaging system 1 according to this embodiment, in a case in which the capture of an ultrasound image ends, the user inputs a command to release the compression through the operation unit 26 of the mammography apparatus 10. In a case in which the command to release the compression has been input through the operation unit 26, the control unit 80 according to this embodiment determines that the capture of an ultrasound image has ended.

In a case in which the capture of an ultrasound image has not ended, that is, in a case in which the command to release the compression has not been input, the determination result in Step S118 is "No". On the other hand, in a case in which the capture of an ultrasound image has ended, that is, in a case in which the command to release the compression has been input, the determination result in Step S118 is "Yes" and the process proceeds to Step S120.

In Step S120, the control unit 80 determines whether or not the current position of the radiation source 36R is the imaging position for CC imaging. In this embodiment, the imaging position for CC imaging is set as the initial position of the radiation source 36R. Therefore, in this step, it is determined whether or not the current position of the radiation source 36R is the initial position. In a case in which the current position of the radiation source 36R is the imaging position for CC imaging, the determination result in Step S120 is "Yes" and the radiation source position control process ends. On the other hand, in a case in which the current position of the radiation source 36R is not the imaging position for CC imaging, that is, in a case in which the current position of the radiation source 36R is the imaging position for MLO imaging, the determination result in Step S120 is "No" and the process proceeds to Step S122.

In Step S122, the control unit 80 directs the radiation source moving unit 37 to move the radiation source 36R to the imaging position of CC imaging and then ends the radiation source position control process.

A method for determining whether or not to capture an ultrasound image in Step S104 of the radiation source position control process in the control unit 80 is not limited to the above-mentioned method. For example, a method according to the following Modification Examples 1 to 3 may be applied.

Modification Example 1

The control unit 80 of the mammography apparatus 10 transmits an inquiry whether or not to capture an ultrasound image to the console 12 and determines to capture an ultrasound image in a case in which a command to capture an ultrasound image is received as the result of the inquiry.

Modification Example 2

The control unit 80 may determine whether or not to capture an ultrasound image on the basis of the amount of mammary gland in the breast as an object. In many cases, the capture of an ultrasound image is performed in a mammary gland region in which mammary gland tissues are likely to overlap each other. Therefore, an ultrasound image can be captured in a case in which the amount of mammary gland is relatively large.

Figure 10:
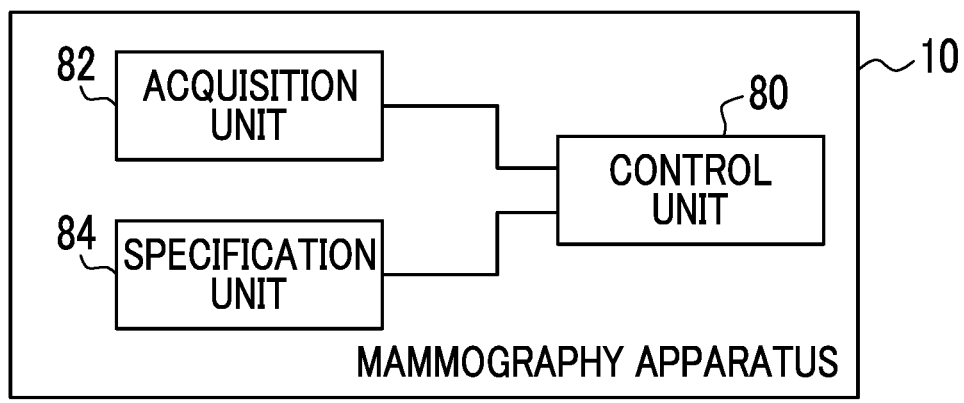
FIG. 10 is a functional block diagram illustrating an example of the function of mammography apparatuses according to Modification Examples 2 and 3.

FIG. 10 is a functional block diagram illustrating an example of the configuration of a mammography apparatus 10 according to this modification example. The mammography apparatus 10 illustrated in FIG. 10 is different from the mammography apparatus 10 illustrated in FIG. 5 in that it further comprises an acquisition unit 82. For example, in the mammography apparatus 10 according to this modification example, the CPU 20A of the control unit 20 executes the radiation source position control processing program 21 stored in the ROM 20B such that the control unit 20 functions as the acquisition unit 82.

The acquisition unit 82 acquires mammary gland amount information indicating the amount of mammary gland from the radiographic image captured by the radiation detector 30 and outputs the acquired mammary gland amount information to the control unit 80. In addition, for example, the amount of mammary gland may be derived from the radiographic image by the radiation detector 30 or the acquisition unit 82. A method for deriving the amount of mammary gland in the breast is not particularly limited. For example, a known method, such as a technique that estimates a mammary gland content on the basis of a radiographic image and a fat image estimated from the radiographic image described in JP2010-253245A, may be used as the method for deriving the amount of mammary gland from the radiographic image.

The control unit 80 receives the mammary gland amount information from the acquisition unit 82. The control unit 80 determines whether or not to capture an ultrasound image on the basis of the input mammary gland amount information. For example, in this modification example, in a case in which the amount of mammary gland indicated by the mammary gland amount information is equal to or greater than a mammary gland amount threshold value, an ultrasound image is captured since the amount of mammary gland is large. Further, for example, the mammary gland amount threshold value used for the determination by the control unit 80 may be experimentally obtained in advance. For example, the mammary gland amount threshold value may vary depending on the thickness of the breast.

Figure 11:
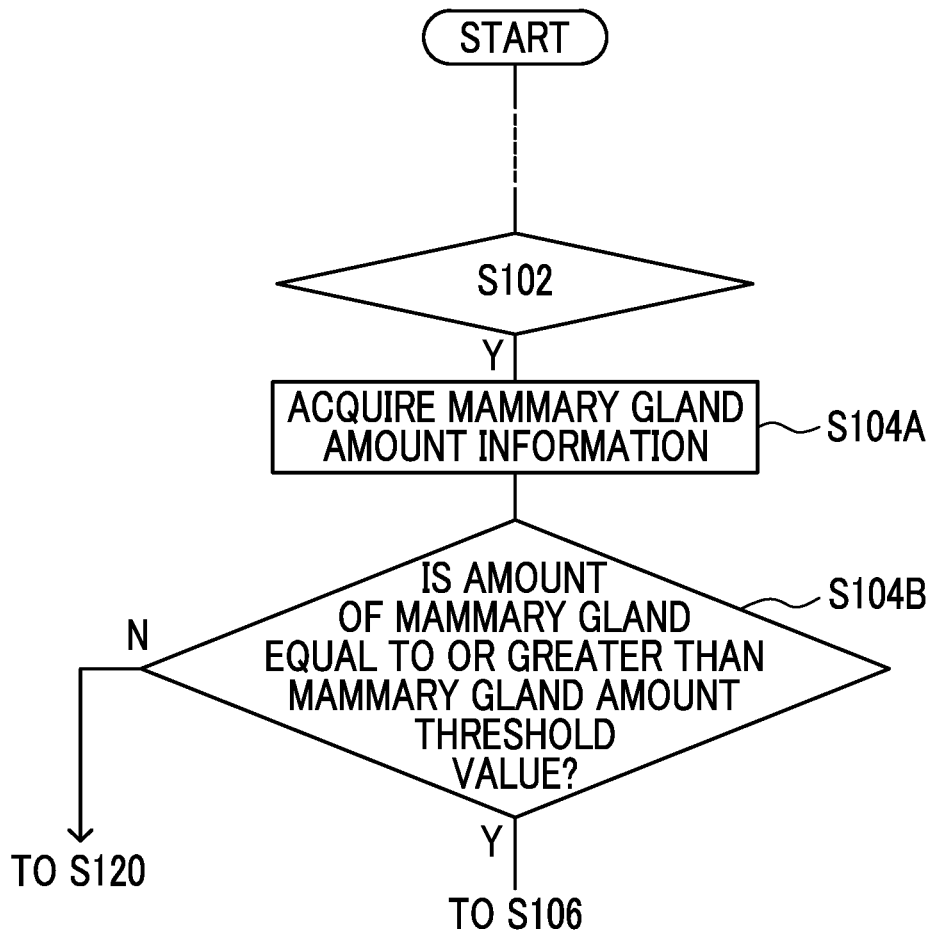
FIG. 11 is a flowchart illustrating an example of the flow of a radiation source position control process of the mammography apparatus according to Modification Example 2.

FIG. 11 illustrates a portion of a flowchart showing an example of the flow of a radiation source position control process of the mammography apparatus 10 according to this modification example. As illustrated in FIG. 11, the radiation source position control process according to this modification example is different from the radiation source position control process (see FIG. 8) according to this embodiment in that each process in Steps S104A and S104B is performed instead of Step S104.

In Step S104A of FIG. 11, the acquisition unit 82 acquires the mammary gland amount information and outputs the acquired mammary gland amount information to the control unit 80 as described above.

Then, in Step S104B, the control unit 80 determines whether or not the amount of mammary gland indicated by the mammary gland amount information is equal to or greater than the mammary gland amount threshold value. In a case in which the amount of mammary gland is equal to or greater than the mammary gland amount threshold value, the determination result in Step S104B is "Yes" and the process proceeds to Step S106 (see FIG. 8). On the other hand, in a case in which the amount of mammary gland is not equal to or greater than the mammary gland amount threshold value, that is, in a case in which the amount of mammary gland is less than the mammary gland amount threshold value, the determination result in Step S104B is "No" and the process proceeds to Step S120 (see FIG. 8).

Modification Example 3

The control unit 80 may determine whether or not to capture an ultrasound image on the basis of the mammary gland region of the breast as an object. As the amount of mammary gland becomes larger, the size of the mammary gland region tends to become larger. As described in Modification Example 2, in many cases, the capture of an ultrasound image is performed for the mammary gland region in which the mammary gland tissues are likely to overlap each other. Therefore, an ultrasound image can be captured in a case in which the amount of mammary gland is relatively large.

The configuration of the mammography apparatus 10 according to this modification example comprises the acquisition unit 82, similarly to the mammography apparatus 10 (see FIG. 10) according to Modification Example 2.

The acquisition unit 82 acquires region information indicating the mammary gland region in the breast from the radiographic image captured by the radiation detector 30 and outputs the acquired region information to the control unit 80. The size of the mammary gland region may be derived from the radiographic image by, for example, the radiation detector 30 or the acquisition unit 82. A method for deriving the mammary gland region in the breast is not particularly limited. For example, mammary gland tissue pixels corresponding to the mammary gland tissues can be detected from the radiographic image and a region in which the number of detected mammary gland tissue pixels is equal to or greater than a predetermined value can be derived as the mammary gland region. A method for detecting the mammary gland tissue pixel is not particularly limited. For example, a technique described in JP2010-253245A can be applied. In a case in which the technique described in this patent publication is applied, first, a radiographic image is divided into a breast image and a direct region. For example, a technique described in JP2010-253245A can be applied. Then, the pectoral muscle region is removed from the breast image. Then, in the breast image from which the pectoral muscle region has been removed, a pixel in which the amount of transmission of the radiation R is equal to or less than a threshold value is detected as the mammary gland tissue region pixel.

The control unit 80 receives the region information from the acquisition unit 82. The control unit 80 determines whether or not to capture an ultrasound image on the basis of the input region information. For example, in this modification example, in a case in which the size of the mammary gland region indicated by the region information is equal to or greater than a region threshold value, an ultrasound image is captured since the amount of mammary gland is large. Further, for example, the region threshold value used for the determination by the control unit 80 may be experimentally obtained in advance. In addition, for example, the region threshold value may vary depending on the thickness of the breast.

Figure 12:
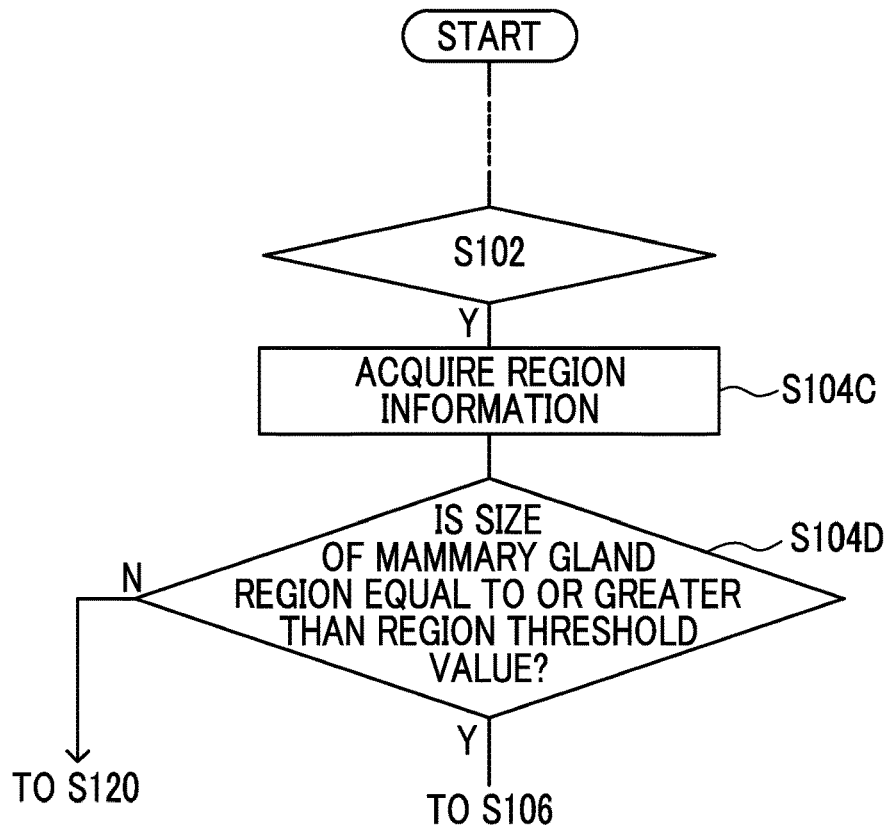
FIG. 12 is a flowchart illustrating an example of the flow of a radiation source position control process of the mammography apparatus according to Modification Example 3.

FIG. 12 illustrates a portion of a flowchart showing an example of the flow of a radiation source position control process of the mammography apparatus 10 according to this modification example. As illustrated in FIG. 12, the radiation source position control process according to this modification example is different from the radiation source position control process (see FIG. 8) according to this embodiment in that each process in Steps S104C and S104D is performed instead of Step S104.

In Step S104C of FIG. 12, the acquisition unit 82 acquires the region information and outputs the acquired region information to the control unit 80, as described above.

Then, in Step S104D, the control unit 80 determines whether or not the size of the mammary gland region indicated by the region information is equal to or greater than the region threshold value. In a case in which the size of the mammary gland region is equal to or greater than the region threshold value, the determination result in Step S104D is "Yes" and the process proceeds to Step S106 (see FIG. 8). On the other hand, in a case in which the size of the mammary gland region is not equal to or greater than the region threshold value, that is, in a case in which the size of the mammary gland region is less than the region threshold value, the determination result in Step S104D is "No" and the process proceeds to Step S120 (see FIG. 8).

Second Embodiment

Next, a second embodiment will be described in detail. In the first embodiment, the aspect in which the types of imaging used to capture the radiographic image are the CC imaging and the MLO imaging has been described. However, in this embodiment, a case in which the types of imaging used to capture the radiographic image further include tomosynthesis imaging will be described.

Figure 13:
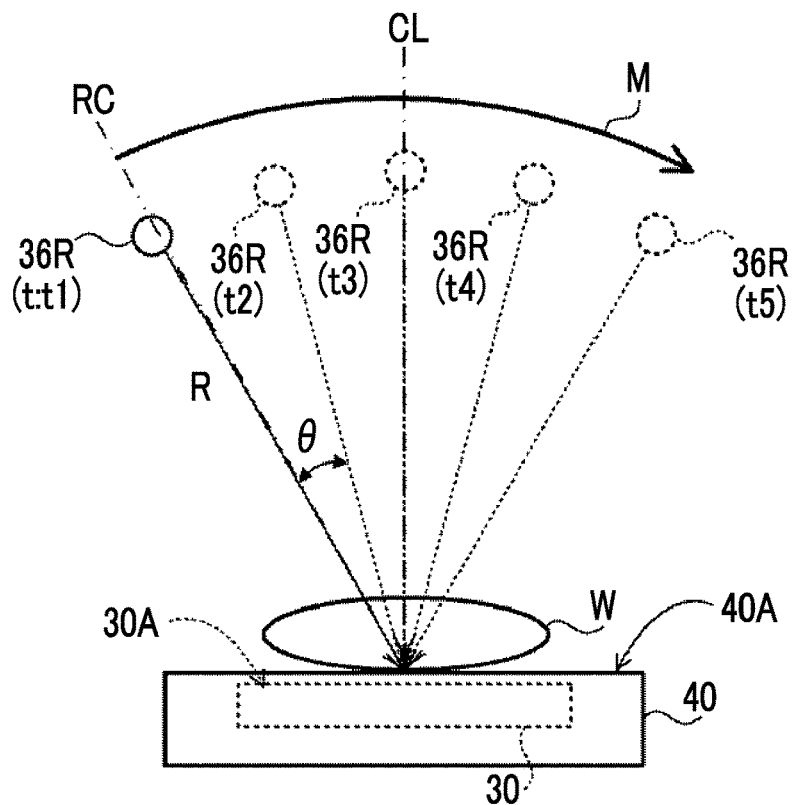
FIG. 13 is a diagram illustrating tomosynthesis imaging performed by a mammography apparatus according to a second embodiment.

The tomosynthesis imaging performed by the mammography apparatus 10 will be described with reference to FIG. 13. In a case in which the mammography apparatus 10 performs the tomosynthesis imaging, with the rotation of the arm portion 42 (see FIG. 3), the radiation source 36R of the radiation emitting unit 36 is continuously moved to each of a plurality of imaging positions t with different irradiation angles (projection angles) by the radiation source moving unit 37. In this embodiment, as illustrated in FIG. 13, the radiation source 36R is moved to the imaging positions t (t1 to tT; T=5 in FIG. 13) with different irradiation angles which are arranged at an interval of a predetermined angle θ, that is, the positions where the radiation R is incident on the detection surface 30A of the radiation detector 30 at different angles. In the example illustrated in FIG. 13, the movement direction M of the radiation source 36R is a direction from the imaging position t1 on the left side to the imaging position t5 on the right side of the subject. The incident angle means an angle formed between the normal line CL to the imaging surface 40A of the imaging table 40 (the detection surface 30A of the radiation detector 30) and the radiation axis RC.

At each imaging position t, the radiation R is emitted from the radiation source 36R to the breast W in response to a command from the console 12 and the radiation detector 30 captures a radiographic image. In a case in which the radiography system 2 performs the tomosynthesis imaging that moves the radiation source 36R to each imaging position t and captures a projection image at each imaging position t, T projection images are obtained.

As illustrated in FIG. 13, in the tomosynthesis imaging, a plurality of projection images are captured. However, the imaging position t of the radiation source 36R in the capture of the final projection image is a non-facing position with respect to the imaging table 40. Therefore, in the mammography apparatus 10 according to this embodiment, in a case in which the capture of a radiographic image in the continuous imaging is tomosynthesis imaging, the retreat position of the radiation source 36R is set as the last imaging position tT (the imaging position t5 in FIG. 13).

Since the configuration of the medical imaging system 1 (see FIG. 1) and the configuration of the radiography system 2 (see FIG. 2) in this embodiment are the same as those in the first embodiment, the description thereof will not be repeated. Since an example of the functional configuration of the mammography apparatus 10 according to this embodiment is the same as that of the mammography apparatus 10 (see FIG. 5) according to the first embodiment, the description thereof will not be repeated.

Figure 14A:
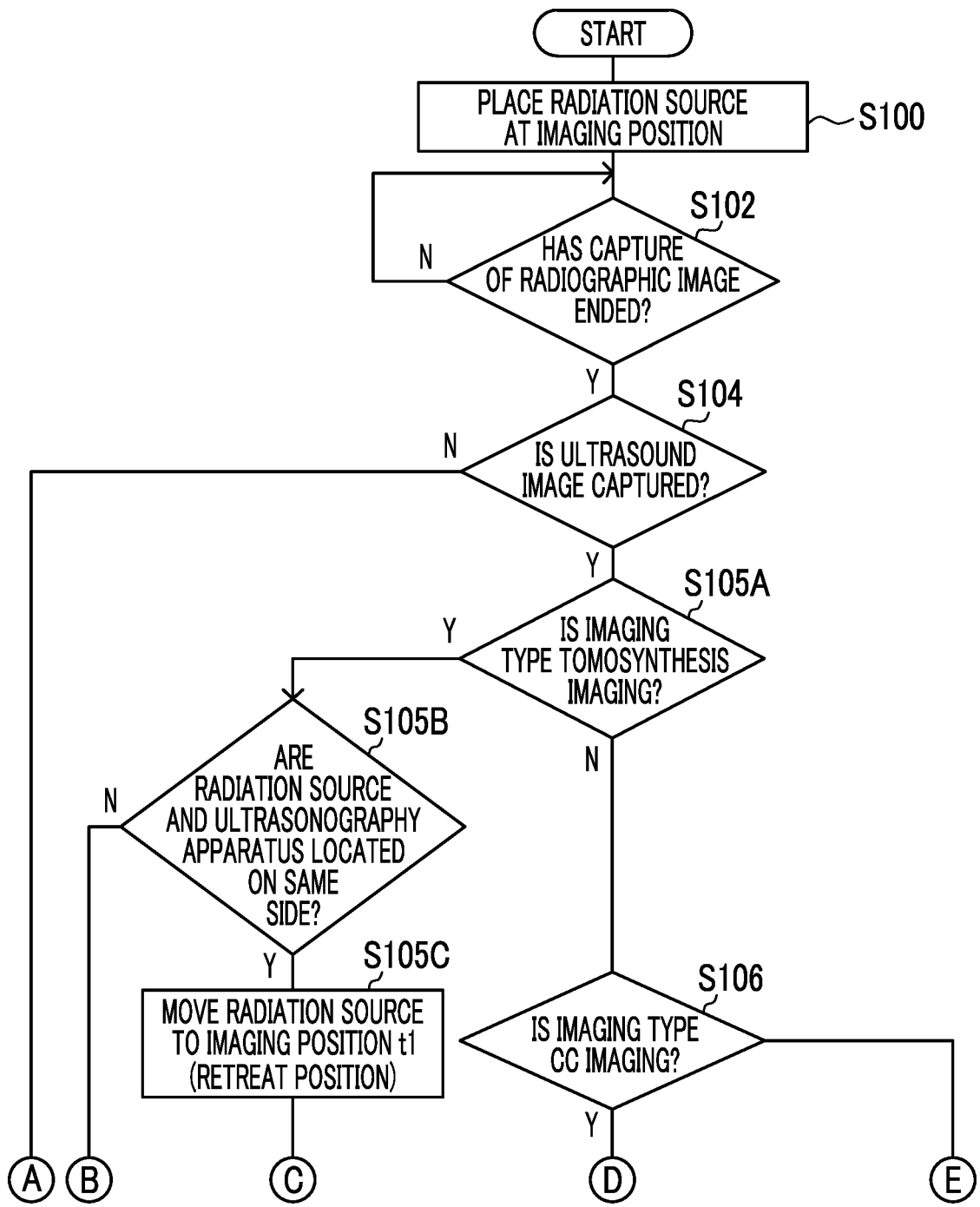
FIG. 14A and FIG. 14B are flowcharts illustrating an example of the flow of a radiation source position control process of the mammography apparatus according to the second embodiment.
Figure 14B:
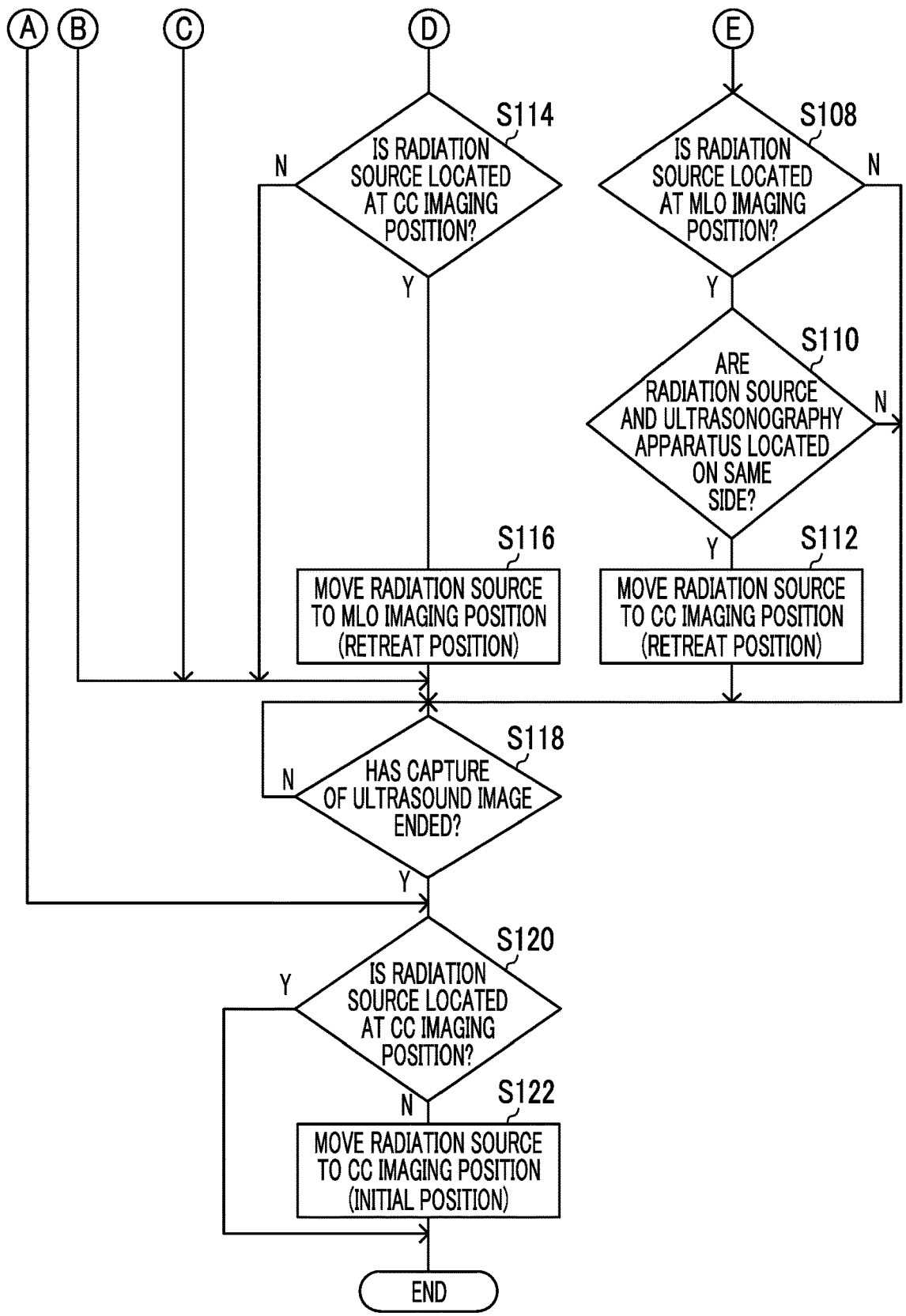

In contrast, since the radiation source position control process according to this embodiment is partially different from the radiation source position control process according to the first embodiment (see FIG. 8), the radiation source position control process according to this embodiment will be described. FIG. 14A and FIG. 14B illustrate a portion of a flowchart showing an example of the flow of a radiation source position control process of the mammography apparatus 10 according to this embodiment. As illustrated in FIG. 14A and FIG. 14B, the radiation source position control process according to this embodiment is different from the radiation source position control process according to the first embodiment (see FIG. 8) in that each process in Steps S105A to S105C is performed after the determination result in Step S104 is "Yes".

As illustrated in FIG. 14A and FIG. 14B, in this embodiment, in a case in which the determination result in Step S104 is "Yes", the process proceeds to Step S105A. In Step S105A, the control unit 80 determines whether or not the type of imaging used to capture the radiographic image which has been performed first is tomosynthesis imaging. In a case in which the type of imaging is not the tomosynthesis imaging, that is, in a case in which the type of imaging is the CC imaging or the MLO imaging, the determination result in Step S105A is "No" and the process proceeds to Step S106. On the other hand, in a case in which the type of imaging is the tomosynthesis imaging, the determination result in Step S105A is "Yes" and the process proceeds to Step S105B.

In Step S105B, the control unit 80 determines whether or not the radiation source 36R and the ultrasonography apparatus 16 are on the same side as in Step S110 which has been described above.

In a case in which the radiation source 36R and the ultrasonography apparatus 16 at the imaging position tT (the imaging position t5 in FIG. 13) are on the same side with respect to the left and right sides of the subject, the radiation source 36R may hinder the user who operates the ultrasound probe 65 of the ultrasonography apparatus 16, as described in the first embodiment. Therefore, in this embodiment, in a case in which the radiation source 36R and the ultrasonography apparatus 16 at the imaging position tT are on the same side, the imaging position tT is not set as the retreat position even though the radiation source 36R is at the non-facing position with respect to the ultrasonography apparatus 16. In this case, for example, in this embodiment, the initial imaging position t1 (see FIG. 13) in the tomosynthesis imaging is set as the retreat position.

In a case in which the radiation source 36R and the ultrasonography apparatus 16 are not on the same side, the determination result in Step S105B is "No" and the process proceeds to Step S118. On the other hand, in a case in which the radiation source 36R and the ultrasonography apparatus 16 are on the same side, the determination result in Step S105B is "Yes" and the process proceeds to Step S105C.

In Step S105C, as described above, the control unit 80 directs the radiation source moving unit 37 to move the radiation source 36R to the initial imaging position t1 in the tomosynthesis imaging, which is the retreat position in a case in which the radiation source 36R and the ultrasonography apparatus 16 are on the same side at the imaging position tT, and proceeds to Step S118.

The retreat position in the tomosynthesis imaging is not limited to the above-mentioned position. For example, a position according to the following Modification Example 4 may be applied.

Modification Example 4

In the above description, the retreat position is the imaging position tT in a case in which the last imaging position tT in the tomosynthesis imaging and the ultrasonography apparatus 16 are not on the same side. In contrast, in this modification example, the retreat position in a case in which the last imaging position tT in the tomosynthesis imaging and the ultrasonography apparatus 16 are not on the same side is set as a position where the inclination angle of the radiation axis RC with respect to the imaging surface 40A of the imaging table 40 is larger than that at the imaging position tT. In other words, in a case in which the last imaging position tT in the tomosynthesis imaging and the ultrasonography apparatus 16 are not on the same side, the control unit 80 increases the inclination angle of the radiation source 36R from the current position of the radiation source 36R.

Figure 15:
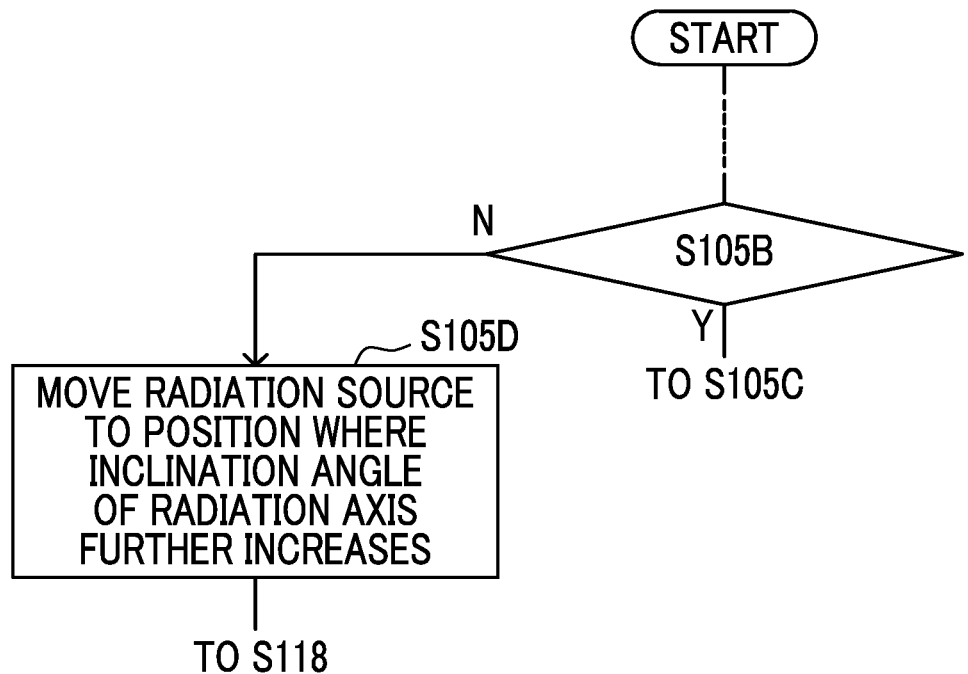
FIG. 15 is a flowchart illustrating an example of the flow of a radiation source position control process of a mammography apparatus according to Modification Example 4.

FIG. 15 illustrates a portion of a flowchart showing an example of the flow of a radiation source position control process of the mammography apparatus 10 according to this modification example. As illustrated in FIG. 15, the radiation source position control process according to this modification example is different from the radiation source position control process according to this embodiment (see FIG. 14A and FIG. 14B) in that a process in Step S105D is performed after the determination result in Step S105B is "No".

As illustrated in FIG. 15, in this modification example, in a case in which the determination result in Step S105B is "No", the process proceeds to Step S105D. In Step S105D, the control unit 80 directs the radiation source moving unit 37 to move the radiation source 36R to a position where the inclination angle of the radiation axis RC with respect to the imaging surface 40A is further increased, as described above.

According to the mammography apparatus 10 of this modification example, the control unit 80 sets the radiation source 36R at a position farther away from the user who takes an ultrasound image. Therefore, the user can easily take ultrasound images.

Third Embodiment

Next, a third embodiment will be described in detail. In this embodiment, an aspect in which the control unit 80 controls the position of the radiation source 36R in a case in which an ultrasound image is captured in the continuous imaging on the basis of correspondence relationship information indicating a correspondence relationship between the type of imaging used to capture the radiographic image and the retreat position will be described.

Figure 16:
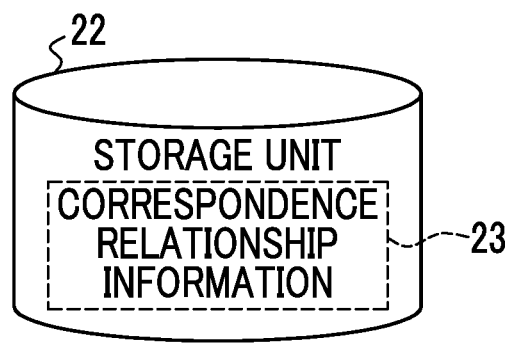
FIG. 16 is a diagram illustrating the configuration of a storage unit in a mammography apparatus according to a third embodiment.

Since the overall configuration of a medical imaging system 1 according to this embodiment (see FIG. 1) is the same as that in the first embodiment, the description thereof will not be repeated. In contrast, the configuration of a radiography system 2 differs from the configuration of the radiography system 2 according to the first embodiment (see FIG. 2) in a portion of the configuration of the mammography apparatus 10. As illustrated in FIG. 16, a storage unit 22 of the mammography apparatus 10 according to this embodiment differs from the storage unit 22 according to the first embodiment in that it stores correspondence relationship information 23 indicating the correspondence relationship between the type of imaging used to capture the radiographic image in the continuous imaging and the retreat position. The correspondence relationship information 23 according to this embodiment is an example of correspondence relationship information according to the present disclosure.

FIG. 17 illustrates an example of the correspondence relationship information 23 according to this embodiment. The correspondence relationship information 23 illustrated in FIG. 17 is information indicating the correspondence relationship among the type of imaging, the position of the ultrasonography apparatus 16, and the retreat position. As described above, it is preferable to determine the retreat position according to the ultrasonography apparatus 16. Therefore, in this embodiment, the correspondence relationship information 23 is information indicating the correspondence relationship of the retreat position that also corresponds to the position of the ultrasonography apparatus 16. As described in the second embodiment, the correspondence relationship information 23 illustrated in FIG. 17 shows an aspect in which the radiation source 36R is moved from the left side to the right side of the subject in the tomosynthesis imaging.

As shown in the correspondence relationship information 23, in a case in which the type of imaging used to capture the radiographic image is the CC imaging and the ultrasonography apparatus 16 is located on the left side of the subject, the retreat position is an imaging position where the MLO imaging is performed for the right breast of the subject. In a case in which the type of imaging used to capture the radiographic image is the CC imaging and the ultrasonography apparatus 16 is located on the right side of the subject, the retreat position is an imaging position where the MLO imaging is performed for the left breast of the subject. In a case in which the type of imaging used to capture the radiographic image is the MLO imaging, the retreat position is an imaging position where the CC imaging is performed, regardless of the position of the ultrasonography apparatus 16. In a case in which the type of imaging used to capture the radiographic image is the tomosynthesis imaging and the ultrasonography apparatus 16 is located on the left side of the subject, the retreat position is the last imaging position tT in the tomosynthesis imaging. Further, in a case in which the type of imaging used to capture the radiographic image is the tomosynthesis imaging and the ultrasonography apparatus 16 is located on the right side of the subject, the retreat position is the initial imaging position t1 in the tomosynthesis imaging.

Figure 18:
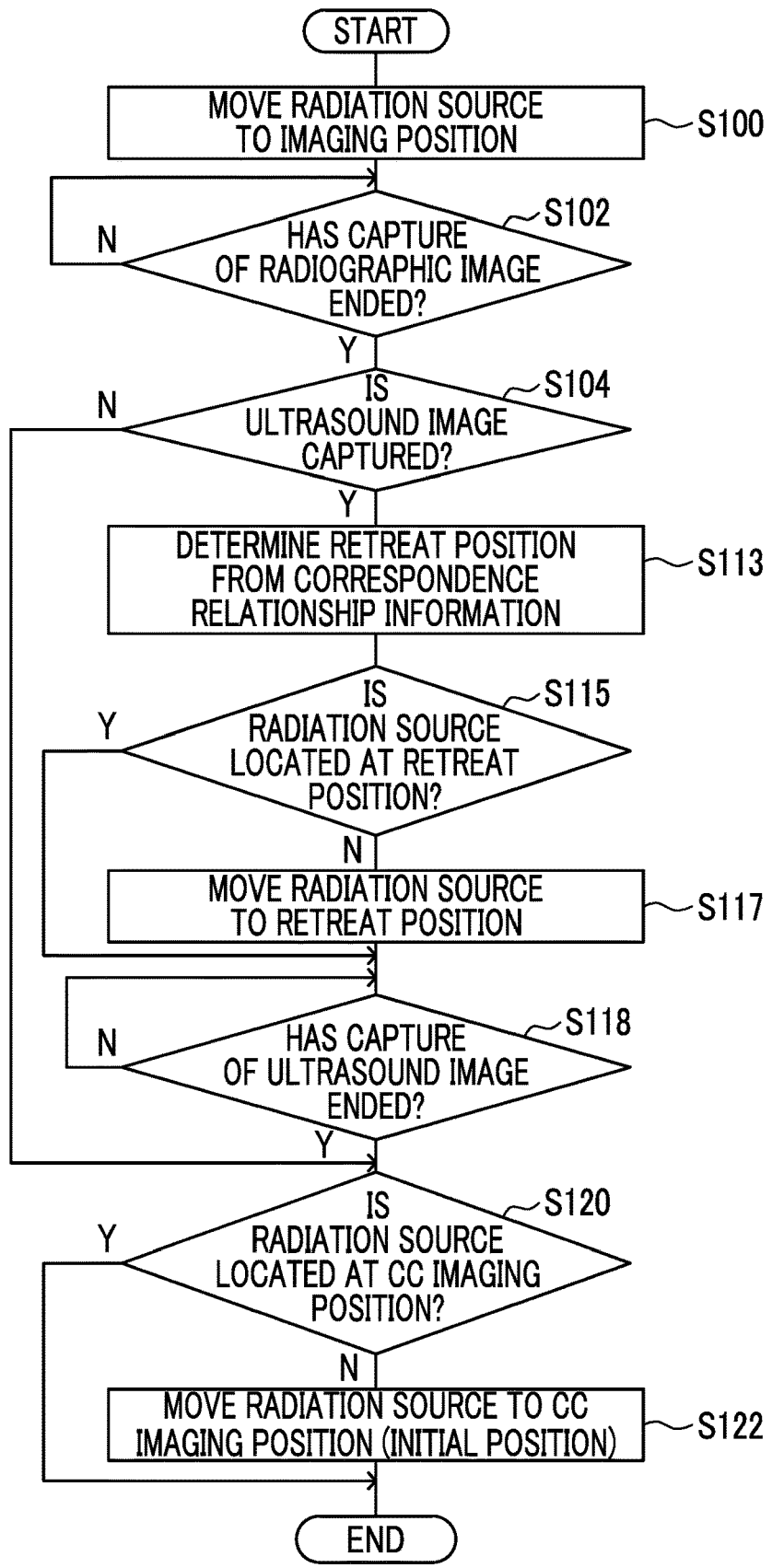
FIG. 18 is a flowchart illustrating an example of the flow of a radiation source position control process of the mammography apparatus according to the third embodiment.

FIG. 18 illustrates a portion of a flowchart showing an example of the flow of a radiation source position control process of the mammography apparatus 10 according to this embodiment. As illustrated in FIG. 18, the radiation source position control process according to this embodiment is different from the radiation source position control process according to the first embodiment (see FIG. 8) in that each process in Steps S113 to S117 is performed instead of Steps S106 to S116.

As illustrated in FIG. 18, in this embodiment, in a case in which the determination result in Step S104 is "Yes", the process proceeds to Step S113. In Step S113, the control unit 80 specifies a retreat position corresponding to the type of imaging used to capture the radiographic image and the position of the ultrasonography apparatus 16 specified by the specification unit 84 from the correspondence relationship information 23 stored in the storage unit 22. For example, as described above, in a case in which the type of imaging used to capture the radiographic image is the CC imaging and the position of the ultrasonography apparatus 16 specified by the specification unit 84 is on the right side of the subject, an imaging position where the MLO imaging is performed for the left breast of the subject is specified as the retreat position.

Then, in Step S115, the control unit 80 determines whether or not the current position of the radiation source 36R is the retreat position specified in Step S113. In a case in which the current position of the radiation source 36R is the retreat position, the determination result in Step S115 is "No" and the process proceeds to Step S118. On the other hand, in a case in which the current position of the radiation source 36R is not the retreat position, the determination result in Step S115 is "Yes" and the process proceeds to Step S117.

In Step S117, the control unit 80 moves the radiation source 36R to the retreat position specified in Step S113 and then proceeds to Step S118.

Figures 19, 20:
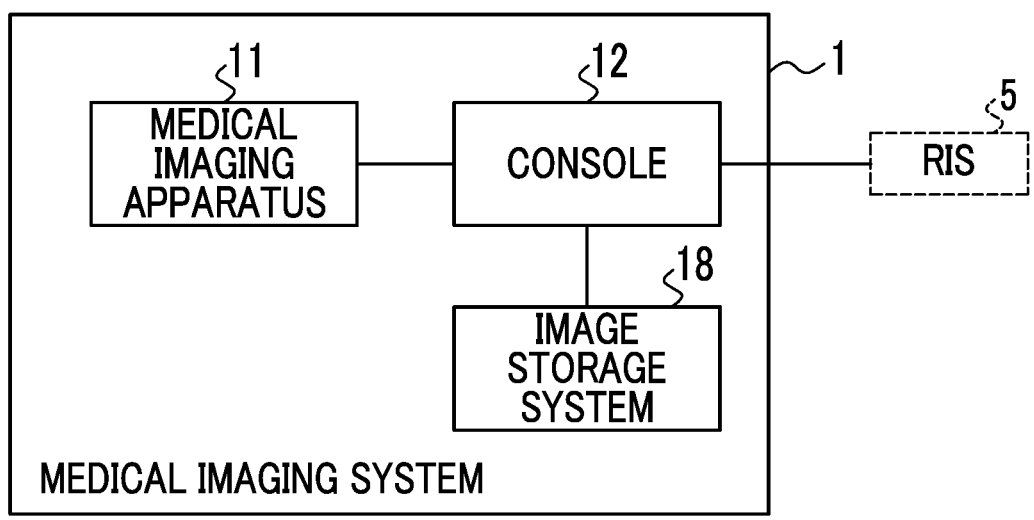
FIG. 19 is a diagram illustrating another example of the correspondence relationship information according to the third embodiment.
FIG. 20 is a diagram schematically illustrating an example of the overall configuration of a medical imaging system according to a fourth embodiment.

Correspondence relationship information 23A indicating the correspondence relationship between the type of imaging and the non-facing position, whose example is illustrated in FIG. 19, may be used instead of the correspondence relationship information 23 which is information indicating the correspondence relationship among the type of imaging, the position of the ultrasonography apparatus 16, and the retreat position.

In this case, the "retreat position" in Steps S113 and S115 of the above-mentioned radiation source position control process (see FIG. 18) may be set as the "non-facing position". Specifically, in Step S113, the control unit 80 specifies a non-facing position corresponding to the type of imaging used to capture the radiographic image from the correspondence relationship information 23A stored in the storage unit 22. Further, in Step S115, the control unit 80 determines whether or not the current position of the radiation source 36R is the non-facing position specified in Step S113.

In addition, as described above, it is preferable that the radiation source 36R and the ultrasonography apparatus 16 are not on the same side. Therefore, in a case in which the current position of the radiation source 36R is the non-facing position and the determination result in Step S113 is "Yes", the control unit 80 determines whether or not the position of the ultrasonography apparatus 16 specified by the specification unit 84 and the radiation source 36R are on the same side. In a case in which the position of the ultrasonography apparatus 16 and the radiation source 36R are on the same side, it is preferable to move the radiation source 36R to a position opposite to the ultrasonography apparatus 16 on the left and right sides of the subject.

Fourth Embodiment

Next, a fourth embodiment will be described in detail. FIG. 20 is a diagram illustrating an example of the overall configuration of a medical imaging system 1 according to this embodiment. As illustrated in FIG. 20, the medical imaging system 1 according to this embodiment differs from the medical imaging system 1 according to the first embodiment (see FIG. 1) in that it comprises a medical imaging apparatus 11 instead of the mammography apparatus 10 and the ultrasonography apparatus 16.

The medical imaging apparatus 11 is an apparatus that is configured by combining the mammography apparatus 10 and the ultrasonography apparatus 16 according to the first embodiment, that is, an apparatus that can capture a radiographic image and an ultrasound image of the breast. For example, the medical imaging apparatus 11 according to this embodiment is a mammography apparatus that can capture an ultrasound image.

Figure 21:
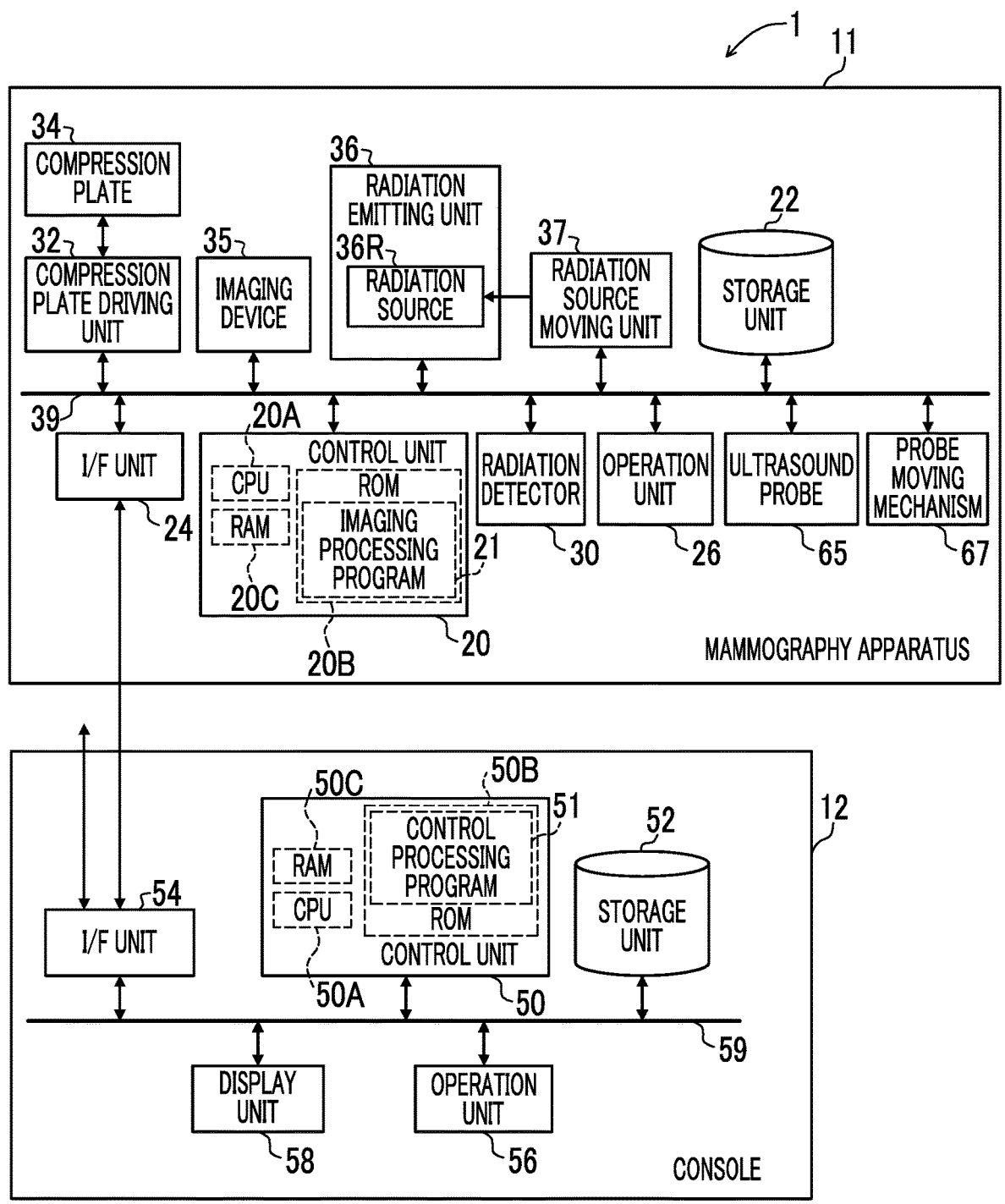
FIG. 21 is a block diagram illustrating an example of the configuration of a console and a medical imaging apparatus according to the fourth embodiment.

FIG. 21 is a block diagram illustrating an example of the configuration of the medical imaging apparatus 11 and the console 12 according to this embodiment. As illustrated in FIG. 21, the medical imaging apparatus 11 according to this embodiment differs from the mammography apparatus 10 according to the first embodiment in that it further comprises an ultrasound probe 65. The ultrasound probe 65 included in the medical imaging apparatus 11 is a so-called handheld type, like the ultrasound probe 65 according to each of the above-described embodiments. The user can operate the ultrasound probe 65 to capture an ultrasound image. For example, in the medical imaging apparatus 11 according to this embodiment, the ultrasound probe 65 is attachably and detachably provided in the mammography apparatus 10. For example, the ultrasound probe 65 is attachable to and detachable from the arm portion 42.

Since the functional configuration of the medical imaging apparatus 11 is the same as the functional configuration of the mammography apparatus 10 according to the first embodiment (see FIG. 5), the description thereof will not be repeated. Since a radiation source position control process performed by the control unit 80 of the medical imaging apparatus 11 according to this embodiment is the same as the radiation source position control process (see FIG. 8) performed by the control unit 80 according to the first embodiment, the description thereof will not be repeated.

As described above, the ultrasound probe 65 included in the medical imaging apparatus 11 according to this embodiment is a so-called handheld type. Therefore, in a case in which an ultrasound image is captured after a radiographic image is captured in the continuous imaging, the radiation source 36R may hinder the user who operates the ultrasound probe 65, as in the medical imaging system 1 according to each of the above-described embodiments.

Therefore, in the medical imaging apparatus 11 according to this embodiment, the control unit 80 performs the radiation source position control process as in the first embodiment, which makes it possible to easily capture an ultrasound image.

Further, in this embodiment, since the medical imaging apparatus 11 has a function of capturing an ultrasound image, the overall size of the apparatus can be less than that in a case in which the mammography apparatus 10 and the ultrasonography apparatus 16 are separately provided.

As described above, the mammography apparatus 10 or the medical imaging apparatus 11 according to each of the above-described embodiments comprises the control unit 80. The control unit 80 performs control to locate the radiation source 36R at the non-facing position where the radiation source 36R and the imaging table 40 do not face each other in a case in which continuous imaging that irradiates the breast of the subject with the radiation R emitted from the radiation source 36R to capture a radiographic image in a compressed state in which the breast is compressed against the imaging table 40 by the compression plate 34 and then captures an ultrasound image of the breast in the compressed state is performed.

In the mammography apparatus 10 or the medical imaging apparatus 11 according to the above-described embodiments, in a case in which an ultrasound image is captured in the continuous imaging, the above-mentioned configuration makes it possible to set the position of the radiation source 36R as a position where the radiation source 36R does not hinder the user who operates the ultrasound probe 65. Therefore, according to the mammography apparatus 10 of each of the above-described embodiments, it is possible to easily capture an ultrasound image.

In addition, in a case in which it is difficult to capture an ultrasound image, the time required for capturing an ultrasound image increases and the time for which the breast of the subject breast is continuously compressed increases. Therefore, the burden on the subject is likely to increase. According to the mammography apparatus 10 or the medical imaging apparatus 11 of each of the above-described embodiments, it is possible to suppress an increase in the time required for capturing an ultrasound image and thus to suppress an increase in the burden on the subject.

In each of the above-described embodiments, the mammography apparatus 10 or the medical imaging apparatus 11 comprises the control unit 80 and functions as the control device according to the present disclosure. However, the apparatus comprising the control unit 80 is not limited to each of the above-described embodiments. For example, another apparatus, such as the console 12, in the medical imaging system 1 may have the functions of the control unit 80 and may function as the control device according to the present disclosure.

In each of the above-described embodiments, the position of the radiation source 36R and the position of the ultrasonography apparatus 16 are based on the subject (the position of the subject) and are on the left side or the right side of the subject in order for the user to perform scanning with the ultrasound probe 65 on the upper surface 34A of the compression plate 34 that compresses the breast of the subject. However, the reference of the position of the radiation source 36R and the position of the ultrasonography apparatus 16 is not limited to the subject. For example, the position of the main body of the mammography apparatus 10 may be used. In this case, the positions (side) described as the left and right sides of the subject in each of the above-described embodiments may be replaced with the left and right sides of the main body of the mammography apparatus 10.

Further, in each of the above-described embodiments, the aspect in which the specification unit 84 specifies the position of the ultrasonography apparatus 16 has been described. However, instead of the position of the ultrasonography apparatus 16, the position of the user who captures an ultrasound image may be specified. In this case, in each of the above-described embodiments, the position of the ultrasonography apparatus 16 may be replaced with the position of the user who captures an ultrasound image.

In each of the above-described embodiments, for example, the following various processors can be used as the hardware structure of processing units performing various processes such as the control unit 80, the acquisition unit 82, and the specification unit 84. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the radiation source position control processing program 21 is stored (installed) in the ROM 20B in advance has been described. However, the invention is not limited thereto. The radiation source position control processing program 21 may be recorded on a recording medium, such as a compact disc read only memory (CD-ROM), a digital versatile disc read only memory (DVD-ROM), or a universal serial bus (USB) memory, and then provided. In addition, the radiation source position control processing program 21 may be downloaded from an external apparatus through the network.

For example, the configurations and operations of the medical imaging system 1, the radiography system 2, and the mammography apparatus 10 described in each of the above-described embodiments are illustrative and may be changed according to the situation, without departing from the scope and spirit of the invention. In addition, the above-described embodiments may be appropriately combined with each other.

What is claimed is:

1. A control device comprising:
    a control unit that, in a case in which subsequent imaging that irradiates a breast of a subject with radiation emitted from a radiation source to capture a radiographic image in a compressed state in which the breast is compressed against an imaging table by a compression member and then captures an ultrasound image of the breast in the compressed state using an ultrasonography apparatus is performed, performs control to locate the radiation source such that a position of the ultrasonography apparatus and a position of the radiation source are opposite to each other on left and right sides of the subject.

2. The control device according to claim 1, wherein, in a case in which the position of the ultrasonography apparatus is a position on the right side of the subject and the position of the radiation source is a position on the right side of the subject, the control unit performs control to locate the radiation source on the left side of the subject.

3. The control device according to claim 1, wherein, in a case in which the position of the ultrasonography apparatus is a position on the left side of the subject and the position of the radiation source is a position on the left side of the subject, the control unit performs control to locate the radiation source on the right side of the subject.

4. A control device comprising:
    a control unit that, in a case in which subsequent imaging that irradiates a breast of a subject with radiation emitted from a radiation source to capture a radiographic image in a compressed state in which the breast is compressed against an imaging table by a compression member and then captures an ultrasound image of the breast in the compressed state is performed, performs control to locate the radiation source at a retreat position in which a radiation axis of the radiation source is inclined with respect to the imaging table,
    wherein the control unit specifies a position of an ultrasonography apparatus that captures the ultrasound image,
    wherein the control unit sets a position of the radiation source as a position corresponding to the specified position of the ultrasonography apparatus,
    wherein, in a case in which the radiographic image is captured with the radiation source located at the retreat position, the control unit performs control to maintain the position of the radiation source at an imaging position where the radiographic image has been captured, and
    wherein, in a case in which the position of the ultrasonography apparatus that captures the ultrasound image and the imaging position are the same on left and right sides of the subject, the control unit performs control to locate the radiation source at a position that is opposite to the imaging position on the left and right sides of the subject.

5. The control device according to claim 4, wherein, in a case in which the imaging position is a position on the right side of the subject and the position of the ultrasonography apparatus is a position on the right side of the subject, the control unit performs control to locate the radiation source on the left side of the subject.

6. The control device according to claim 4, wherein, in a case in which a type of imaging used to capture the radiographic image is cranio-caudal imaging, the control unit performs control to locate the radiation source at a position in a case in which the type of imaging used to capture the radiographic image is medio-lateral oblique imaging.

7. The control device according to claim 6, wherein the control unit performs control to locate the radiation source at a position, which is opposite to the position of the ultrasonography apparatus that captures the ultrasound image on left and right sides of the subject, among positions in a case in which the medio-lateral oblique imaging is performed.

8. The control device according to claim 4, wherein, in a case in which capturing the ultrasound image is performed after tomosynthesis imaging by inclining the radiation axis of the radiation source with respect to the imaging table, and
in a case in which the position of the ultrasonography apparatus that captures the ultrasound image is opposite to the position of the radiation source on left and right sides of the subject,
the control unit performs control to maintain the position of the radiation source in a facing position where the radiation source and the imaging table face each other.

9. The control device according to claim 4, wherein the control unit acquires mammary gland amount information indicating an amount of mammary gland in the breast, and
wherein the control unit controls the ultrasonography apparatus to capture the ultrasound image in a case in which the amount of mammary gland indicated by the mammary gland amount information is equal to or greater than a predetermined amount of mammary gland.

10. The control device according to claim 4, wherein the control unit acquires region information indicating a mammary gland region in the breast on the basis of the radiographic image, and
wherein the control unit controls the ultrasonography apparatus to capture the ultrasound image in a case in which a size of the mammary gland region indicated by the region information is equal to or greater than a predetermined size.

11. A radiography system comprising:
a mammography apparatus that includes a radiation source, a radiation detector, and a compression member which is configured to compress a breast disposed between the radiation source and the radiation detector and captures a radiographic image of the breast in the compressed state using the radiation detector; and
the control device according to claim 4, that controls the mammography apparatus.

12. A medical imaging system comprising:
the radiography system according to claim 11; and
the ultrasonography apparatus that captures the ultrasound image of the breast compressed by the compression member of the mammography apparatus included in the radiography system.

13. A medical imaging system comprising:
a medical imaging apparatus that includes a radiation source, a radiation detector, and a compression member which is configured to compress a breast disposed between the radiation source and the radiation detector, captures a radiographic image of the breast in the compressed state using the radiation detector, and captures an ultrasound image of the breast in the compressed state; and
the control device according to claim 4, that controls the medical imaging apparatus.

14. A control method comprising:
in a case in which subsequent imaging that irradiates a breast of a subject with radiation emitted from a radiation source to capture a radiographic image in a compressed state in which the breast is compressed against an imaging table by a compression member and then captures an ultrasound image of the breast in the compressed state is performed, performing control to locate the radiation source at a retreat position in which a radiation axis of the radiation source is inclined with respect to the imaging table;
performing control to specify a position of an ultrasonography apparatus that captures the ultrasound image; and
performing control to set a position of the radiation source as a position corresponding to the specified position of the ultrasonography apparatus,
wherein, in a case in which the radiographic image is captured with the radiation source located at the retreat position, the control method further comprises performing control to maintain the position of the radiation source at an imaging position where the radiographic image has been captured, and
wherein, in a case in which the position of the ultrasonography apparatus that captures the ultrasound image and the imaging position are the same on left and right sides of the subject, the control method further comprises performing control to locate the radiation source at a position that is opposite to the imaging position on the left and right sides of the subject.

15. A non-transitory computer readable medium storing a control program that causes a computer to execute a process, the process comprising:
in a case in which subsequent imaging that irradiates a breast of a subject with radiation emitted from a radiation source to capture a radiographic image in a compressed state in which the breast is compressed against an imaging table by a compression member and then captures an ultrasound image of the breast in the compressed state is performed, performing control to locate the radiation source at a retreat position in which a radiation axis of the radiation source is inclined with respect to the imaging table;
performing control to specify a position of an ultrasonography apparatus that captures the ultrasound image; and
performing control to set a position of the radiation source as a position corresponding to the specified position of the ultrasonography apparatus,
wherein, in a case in which the radiographic image is captured with the radiation source located at the retreat position, the process further comprises performing control to maintain the position of the radiation source at an imaging position where the radiographic image has been captured, and
wherein, in a case in which the position of the ultrasonography apparatus that captures the ultrasound image and the imaging position are the same on left and right sides of the subject, the process further comprises performing control to locate the radiation source at a position that is opposite to the imaging position on the left and right sides of the subject.

* * * * *